US007501116B2

(12) United States Patent
Kiss

(10) Patent No.: US 7,501,116 B2
(45) Date of Patent: *Mar. 10, 2009

(54) PLACENTAL ALKALINE PHOSPHATASE TO CONTROL DIABETES

(75) Inventor: Zoltan Kiss, Austin, MN (US)

(73) Assignee: Zoltan Laboratories, Austin, MN (US)

( * ) Notice: Subject to any disclaimer, the term of this patent is extended or adjusted under 35 U.S.C. 154(b) by 405 days.

This patent is subject to a terminal disclaimer.

(21) Appl. No.: 11/241,068

(22) Filed: Sep. 30, 2005

(65) Prior Publication Data

US 2006/0034818 A1 Feb. 16, 2006

Related U.S. Application Data

(63) Continuation of application No. 10/441,992, filed on May 20, 2003, now Pat. No. 7,014,852, which is a continuation-in-part of application No. 10/317,916, filed on Dec. 12, 2002, now Pat. No. 7,048,914.

(51) Int. Cl.
A61K 38/46 (2006.01)

(52) U.S. Cl. .................................... 424/94.6

(58) Field of Classification Search ........................ None
See application file for complete search history.

(56) References Cited

U.S. PATENT DOCUMENTS

| 4,030,995 | A | 6/1977 | Starkweather |
| 4,306,020 | A | 12/1981 | Meiattini |
| 6,290,952 | B1 | 9/2001 | Poelstra et al. |
| 2002/0037555 | A1 | 3/2002 | Chen |
| 2002/0127216 | A1 | 9/2002 | Kiss |
| 2004/0120940 | A1 | 6/2004 | Kiss |

FOREIGN PATENT DOCUMENTS

| WO | WO 97/47316 | 12/1997 |
| WO | WO 02/072136 A1 | 9/2002 |

OTHER PUBLICATIONS

Schmitz O. et al. Optimizing inslulin secretagogue therapy in patients with Type-2 diabetes: a randomized double-blind study with repaglinide, Diabetes Care, Feb. 2002, 25(2): 342-346, entire document.*
Brock et al., "Measurement of placental alkaline phosphatase in maternal plasma as an indicator of subsequent low birthweight outcome", British Journal of Obstetrics and Gynaecology, Jan. 1988, vol. 95, pp. 769-783.
Bell et al., "Diabetes mellitus and genetically programmed defects in β-cell function", Nature, vol. 414, pp. 788-791, 2001.
Mathis et al., "β-cell death during progression to diabetes", Nature, vol. 414, pp. 792-798, 2001.
Saltiel, "New perspectives into the molecular pathogenesis and treatment of Type II diabetes", Cell, vol. 104, pp. 517-529, 2001.
Zimmet et al., "Global and societal implications of the diabetes epidemic", Nature, vol. 414, pp. 782-787, 2001.
Moller, "New drug targets for Type II diabetes and the metabolic syndrome", Nature, vol. 414, pp. 821-827, 2001.
Ho et al., "Antioxidants, NFxB activation, and diabetogenesis", Proc. Soc. Exp. Biol. Med., vol. 222, pp. 205-213, 1999.
Saltiel et al., "Insulin signaling and the regulation of glucose and lipid metabolism", Nature, vol. 414, pp. 799-806, 2001.
U.K. Prospective Diabetes Study Group, "U.K. Prospective Diabetes Study 16. Overview of 6 years' therapy of Type II diabetes: A progressive disease", Diabetes, vol. 44, pp. 1249-1258, 1995.
Ryan et al., "Successful islet transplantation: Continued insulin reserve provides long-term gylcemic control", Diabetes, vol. 51, pp. 2148-2157, 2002.
Clubb et al., "The behavior of infused human placental alkaline phosphatase in human subjects", J. Lab. & Clin. Med., vol. 66, pp. 493-507, 1965.
Rolin et al., "The long-acting GLP-1 derivative NN2211 ameliorates glycemia and increases β-cell mass in diabetic mice", Am. J. Physiol. Endocrinol. Metab., vol. 283, pp. E745-E752, 2002.
Brownlee, "Biochemistry and molecular cell biology and diabetic complications", Nature, vol. 414, pp. 813-820, 2001.
Chang et al., "Human placenta alkaline phosphatase: An improved purification procedure and kinetic studies", Eur. J. Biochem., vol. 209, pp. 241-247, 1992.
Huang et al., "Focal adhesion kinase (FAK) regulates insulin-stimulated glycogen synthesis in hepatocytes", J. Biol. Chem., vol. 277, pp. 18151-18160, 2002.
Kottel et al., "Differential release of membrane-bound alkaline phosphatase isoenzymes from tumor cells by bromelain", Biochem. Biophys. Methods, vol. 2, pp. 325-330, 1980.
Chang et al., "Modification of human placental alkaline phosphatase by periodate-oxidized 1,$N^6$-ethenoadenosine monophosphate", Biochem. J., vol 272, pp. 683-690, 1990.
She et al., "α-antitrypsin can increase insulin-induced mitogenesis in various fibroblast and epithelial cell lines", FEBS Letters, vol. 473, pp. 33-36, 2000.

(Continued)

Primary Examiner—Irene Marx
Assistant Examiner—Satyendra K Singh
(74) Attorney, Agent, or Firm—Faegre & Benson LLP

(57) ABSTRACT

The present invention provides methods for using human placental alkaline phosphatase or an active derivative to reduce blood glucose level in a mammal. Treatment regimens provided by the invention may be used to control Type 1 and Type 2 forms of diabetes in humans. The methods and treatment regimens may be effective to maintain the human's blood glucose level below about 10 mM, and preferably within the normal range of 4 mM to 7 mM. The methods and treatment regimens may be used in combination with administration of known anti-diabetic medicaments. Also provided by the invention is a method for inducing weight loss or reducing an expected weight gain caused by or associated with obesity or Type 2 diabetes. The invention further provides a preparation for administration to a human, the preparation comprising homogeneous purified human placental alkaline phosphatase in a physiologically acceptable carrier.

18 Claims, 19 Drawing Sheets

OTHER PUBLICATIONS

Lyons et al,. "Mapping by Genetic Interaction: High Resolution congenic mapping of the type 1 diabetes loci Idd10 and Idd18, in the NOD mouse", *Diabetes*, vol. 50, pp. 2633-2637, 2002.

Kaufman et al., "Report from the 1st international NOD mouse T-cell workshop and the follow-up mini-workshop", *Diabetes*, vol. 50, pp. 2451-2458, 2001.

Bonifacio et al., "International Workshop on lessons from animal models for human type 1 diabetes: Identification of insulin but not glutamic acid decarboxylase or IA-2 as specific autoantigens of humoral autoimmunity in nonobese diabetic mice", *Diabetes*, vol. 50, pp. 2451-2458, 2001.

Spiegelman et al., "Obesity and the regulation of energy balance", *Cell*, vol. 104, pp. 531-543, 2001.

Gregoire et al., "Adipocyte differentiation: From fibroblast to endocrine cell", *Exp. Biol. Med.*, vol. 226, pp. 997-2001, 2001.

Lieberman et al., "Identification of the β cell antigen targeted by a prevalent population of pathogenic CD8$^+$ T cells in autoimmune diabetes", *Proc. Natl. Acad. Sci.*, Jul. 8, 2003, pp. 8384-8388, vol. 100, No. 14.

Green et al., "CD4$^+$ CD25$^+$ T regulatory cells control anti-islet CD8$^+$ T cells through TGF-β—TGF-β receptor interactions in type 1 diabetes", *Proc. Natl. Acad. Sci.*, Sep. 16, 2003, pp. 10878-10883, vol. 100, No. 19.

Cao et al., "Pancreatic-Derived Factor (FAM3B), a Novel Islet Cytokine, Induces Apoptosis of Insulin-Secreting β-cells", *Diabetes*, Sep. 2003, pp. 2296-2303, vol. 52, American Diabetes Association.

Ferrannini et al., "β-cell Function in Obesity", *Diabetes*, Dec. 2004, pp. S26-S33, vol. 53, Supplement 3, American Diabetes Association.

Rossini, "Banting Lecture 2003: Autoimmune Diabetes and the Circle of Tolerance", *Diabetes*, Feb. 2004, pp. 267-275, vol. 53, American Diabetes Association.

Butler et al., "β-cell Deficit and Increased β-cell Apoptosis in Humans With Type 2 Diabetes", *Diabetes*, 2003, pp. 102-110, vol. 52.

Chang et al., "Aging and insulin secretion", *Am J Physiol Endocrinol Metab*, Jan. 2003, pp. E7-E12, vol. 284, the American Physiological Society.

Farris et al., "Insulin-degrading enzyme regulates the levels of insulin, amyloid β-protein, and the β-amyloid precursor protein intracellular domain in vivo", *Proc. Natl. Acad. Sci.*, Apr. 1, 2003, pp. 4162-4167, vol. 100, No. 7.

Huopio et al., "A new subtype of autosomal dominant diabetes attributable to a mutation in the gene for sulfonylurea receptor 1", *The Lancet*, Jan. 25, 2003, pp. 301-307, vol. 361.

Hanis et al., "A genome-wide search for human non-insulin-dependent (type 2) diabetes genes reveals a major susceptibility locus on chromosome 2", *Nature Genetics*, Jun. 13, 1996, pp. 161-166, vol. 13.

Weir et al., "Five Stages of Evolving β-cell Dysfunction During Progression to Diabetes", *Diabetes*, Dec. 2004, pp. S16-S20, vol. 53, Supplement 3, the American Diabetes Association.

She et al., "Growth factor-like effects of placental alkaline phosphatase in human fetus and mouse embryo fibroblasts", *FEBS Letters*, vol. 469, pp. 163-167, 2000.

She et al., "Placental alkaline phosphatase, insulin, and adenine nucleotides or adenosine synergistically promote long-term survival of serum-starved mouse embryo and human fetus fibroblasts", *Cellular Signalling*, vol. 12, pp. 659-665, 2000.

Anthony et al., "Signaling Pathways Involved in Translational control of Protein Synthesis in skeletal Muscle by Leucine," *Symposium: Leucine as a Nutritional Signal*, pp. 856S-860S, San Diego, CA, 2001.

Atkinson, "Thirty Years of Investigating the Autoimmune Basis for Type 1 Diabetes," *ADA Outstanding Scientific Achievement Lecture 2004*, 2005.

Baracos, "Management of Muscle Wasting in Cancer-Assoicated Cachexia," *Cancer-Related Fatigue: New Directions for Research*, vol. 192, pp. 1669-16677, 2001.

Barbieri et al., "Chronic inflammation and the effect of IGF-I on muscle strength and power in older persons," *Am J Physiol Endocrinol Metab*, vol. 284, pp. E481-E487, 2003.

Barton-Davis et al., "Viral mediated expression of insulin-like growth factor I blocks the aging-related loss of skeletal muscle function," *Proc. Natl. Acad. Sci. USA*, vol. 95, pp. 15603-15607, 1998.

Beck et al., "Expression of Human Placental alkaline Phosphatase in *Escherichia coli*," *Protein Expression and Purification*, vol. 5, pp 192-197, 1994.

Bottino et al., "Preservation of Human Islet Cell Functional Mass by Anti-Oxidative Action of a Novel SOD Mimic Compound," *Diabetes*, vol. 51, pp. 2561-2567, 2002.

Bottino et al., "Response of Human Islets to Isolation Stress and the Effect of Antioxidant Treatment," *Diabetes*, vol. 53, pp. 2559-2568, 2004.

Brandhorst et al., "Successful Human Islet Isolation Utilizing Recombinant Collagenase," *Diabetes*, vol. 52, pp. 1143-1146, 2003.

Brownlee, "The Pathobiology of Diabetic Complications," *Banting Lecture* 2004, 2005.

Carlevaro et al., "Transferrin Promotes Endothelial Cell Migration and Invasion: Implication in Cartilage Neovascularization," *The Journal of Cell Biology*, vol. 136, No. 6, pp. 1375-1384, 1997.

Carmichael et al., "Evaluation of a Tetrazolium-based Semiautomated Colorimetric Assay: Assessment of Chemosensitivity Testing," *Cancer Research*, vol. 47, pp. 936-942, 1987.

Carroll et al. "Combined growth hormone/insulin-like growth factor I in addition to glutamine-supplemented TPN results in net protein anabolism in critical illness," *Am J Physiol Endocrinol Metab*, vol. 286, pp. E151-E157, 2004.

Cebrian et al., "Overexpression o f Parathyroid Hormone-Related Protein Inhibits Pancreatic β-Cell Death in Vivo and In Vitro," *Diabetes*, vol. 51, pp. 3003-3013, 2002.

Chang et al., "Human placental alkaline phosphatase," *Eur. J. Biochem.* vol. 209, pp. 241-247, 1992.

Chang et al., "Modification of human placental alkaline phophatase by periodate-oxidized 1, N$^6$-ethenoadenosine monophosphate," *Biochem. J.* vol. 272, pp. 683-690, 1990.

Chen et al., "Overespression of Metallothionein in Pancreatic β-Cells Reduces Streptozotocin-Induced DNA Damage and Diabetes," *Diabetes*, vol. 50, pp. 2040-2046, 2001.

De Arcangelis et al., "IGF-induced Differentiation of L6 Myogenic Cells Requires the Activity of cAMP-Phosphodiesterase," *Molecular Biology of the Cell*, vol. 14, pp. 1392-1404, 2003.

De Benedetti et al., "Interleukin 6 Causes Growth Impairment in Transgenic Mice through a Decrease in Insulin-like Growth Factor-I," *J. Clin. Invest.* vol. 99, pp. 643-650, 1997.

Ekblom et al., "Transferrin as a fetal growth factor: Acquisition of responsiveness related to embryonic induction," *Proc. Natl. Acad. Sci. USA*, vol. 80, pp. 2651-2655, 1983.

Eitel et al., "Different role of saturated and unsaturated fatty acids in β-cell apoptosis," *Biochemical and Biophysical Research Communications*, vol. 299, pp. 853-856, 2002.

Eitel et al., "Protein Kinase Cδ Activation and Translocation to the Nucleus Are Required for Fatty Acid-Induced Apoptosis of Insulin-Secreting Cells," *Diabetes*, vol. 52, pp. 991-997 2003.

Ferrando et al., "Testosterone administration to older men improves muscle function: molecular and physiolological mechanisms," *Am J Physiol Endocrinol Metab*, vol. 282, pp. E601-E607, 2002.

Guilherme et al., "Perinuclear Localization and Insulin Responsiveness of GLUT4 Requires Cytoskeletal Integrity in 3T3-L1 Adipocytes," *The Journal of Biological Chemistry*, vol. 275, No. 49, pp. 38151-38159, 2000.

Günther et al., "Carbon Monoxide Protects Pancreatic β-Cells From Apoptosis and Improves Islet Function/Survival After Transplantation," *Diabetes*, vol. 51, pp. 994-999, 2002.

Heimo et al., "Human Placental Alkaline Phosphatase: Expression in *Pichia pastoris*, Purification and Characterization of the Enzyme," *Protein Expression and Purification*, vol. 12, pp. 85-92, 1998.

Ishida, et al., "Pioglitazone Improves Insulin Secretory Capacity and Prevents the Loss of β-Cell Mass in Obese Diabetic db/db Mice: Possible Protection of βCells From Oxidative Stress," *Metabolism*, vol. 53, No. 4, pp. 488-494, 2004.

Kozlenkov et al., "Function Assignment to Conserved Residues in Mammalian Alkaline Phosphatases," *The Journal of Biological Chemistry*, vol. 277, No. 25, pp. 22992-22999, 2002.

Kwon et al., "cAMP Dose-dependently Prevents Palmitate-induced Apoptosis by Both Protein Kinase A- and cAMP-Guanine Nucleotide Exchange Factor-dependent Pathways in β-Cells," *The Journal of Biological Chemistry*, vol. 279, No. 10, pp. 8938-8945, 2004.

Van Leeuwen et al., "The embedded tumour: host physiology is important for the evaluation of tumour growth," *British Journal of Cancer*, vol. 89, pp. 2254-2263, 2003.

De Leon et al., "Role of Endogenous Glucagon-Like Peptide-1 in Islet Regeneration After Partial Pancreatectomy," *Diabetes*, vol. 52, pp. 365-371, 2003.

Li et al., "Betacellulin improves glucose metabolism by promoting conversion of intraislet precursor cells to β-cells in streptozocin-treated mice," *Am J Physiol Endocrinol Metab*, vol. 285, pp. E577-E583, 2003.

Lingohr et al., Activation of IRS-2—Mediated Signal Transduction by IGF-1, but not TGF-α or EGF, Augments Pacreatic β-Cell Proliferation, *Diabetes*, vol. 51, pp. 966-976, 2002.

Lupi et al., "Prolonged Exposure to Free Fatty Acids Has Cytostatic and Pro-Apoptotic Effects on Human Pancreatic Islets," *Diabetes*, vol. 51, pp. 1437-1442, 2002.

Lynch et al., "Leucine is a direct-acting nutrient signal that regulates protein synthesis in adipose tissue," *Am J Physiol Endocrinol Metab*, vol. 283, pp. E503-E513, 2002.

Maedler et al., "Monosaturated Fatty Acids Prevent the Deleterious Effects of Palmitate and High Glucose on Human Pancreatic β-Cell Turnover and Function," *Diabetes*, vol. 52, pp. 726-733, 2003.

Mandrup-Poulsen, "β-Cell Apoptosis," *Diabetes*, vol. 50, pp. S58-S63, 2001.

Mattsson et al., "Decreased Vascular Density in Mouse Pancreatic Islets After Transplantation," *Diabetes*, vol. 51, pp. 1362-1366, 2002.

Millán et al., "Biology of Human Alkaline Phosphatases with Special Reference to Cancer," *Critical Reviews in Clinical Laboratory Sciences*, vol. 32, pp. 1-39, 1995.

Morley et al., "From the Chicago Meetings," *J Lab Clin Med*, vol. 137, pp. 231-243, 2001.

Mysore et al., "Overexpression of Glutathione Peroxidase With Two Isoforms of Superoxide Dismutase Protects Mouse Islets From Oxidative Injury and Improves Islet Graft Function," *Diabetes*, vol. 54, pp. 2109-2116, 2005.

Nielsen et al., "Regulation of β-Cell Mass by Hormones and Growth Factors," *Diabetes*, vol. 50, pp. S25-S29, 2001.

O'Connor, et al., "Insulin and amino acids independently stimulate skeletal muscle protein synthesis in neonatal pigs," *Am J Physiol Endocrinol Metab*, vol. 284, pp. E110-E119, 2003.

Owino et al., "Age-related loss of skeletal muscle function and the inability of express the authocrine form of insulin-like growth factor-1 (MGF) in response to mechanical overload," *FEBS Letters*, vol. 505, pp. 259-263, 2001.

Powis et al., "The Role of the Redox Protein Thioredoxin In Cell Growth And Cancer," *Free Radoca; Biology & Medicine*, vol. 29, Nos. 3/4, pp. 312-322, 2000.

Qian et al., "Targeted Drug Delivery via the Transferrin Receptor-Mediated Endocytosis Pathway," *Pharmacol Rev.*, vol. 54, No. 4, pp. 561-587, 2002.

Robertson et al., "Glucose Toxicity in β-Cells: Type 2 Diabetes, Good Radicals Gone Bad, and the Gluthathione Connection," *Diabetes*, vol. 52, pp. 581-587, 2003.

Rolin et al., "The long-acting GLP-1 derivative NN2211 ameliorates glycemia and increases β-cell mass in diabetic mice," *Am J Physiol Endocrinol Metab*, vol. 283, pp. E745-E752, 2002.

Rooman et al., "Gastrin Stimulates β-Cell Neogenesis and Increases Islet Mass From Transdifferentiated but Not From Normal Exocrine Pancrease Tissue," *Diabetes*, vol. 51, pp. 686-690, 2002.

Ryan et al., "Five-Year Follow-Up After Clinical Islet Transplantation," *Diabetes*, vol. 54, pp. 2060-2069, 2005.

Seale et al., "The Potential of Muscle Stem Cells," *Developmental Cell*, vol. 1, pp. 333-342, 2001.

Tabatabaie et al., "Free Radicals and the Pathogenesis of Type 1 Diabetes," *Diabetes*, vol. 52, pp. 1994-1999, 2003.

Tomiya et al., "Complex-type biantennary *N*-glycans of recombinant human transferring from *Trichoplusia nl* insect cells expressing mammalian β-1, 4-galactosyltransferase and β-1, 2-*N*-acetylglucosaminyltransferase II," *Glycobiology*, vol. 13, No. 1, pp. 23-24, 2003.

Yarasheski, et al. "Effect of growth hormone and resistance exercise on muscle growth and strength in older men," *Am J Physiol*, vol. 268, pp. E268-276, 1995.

Shulman, "Cellular mechanisms of insulin resistance," *Journal of Clinical Investigation*, vol. 106, No. 2, pp. 171-176, 2000.

Holmgren et al., "Serum Levels of Placental Alkaline Phosphatase in High-risk Pregnancies," *Obstet. gynecol.* vol. 54, pp. 631-634, 1979.

Wojcicka-Bentyn, et al., Extremely elevated activity of serum alkaline phosphatase in gestational diabetes: A case report, *American Journal of Obstetrics and Gynecology*, vol. 190, pp. 566-567, 2004.

* cited by examiner

PLACENTAL ALKALINE PHOSPHATASE TO CONTROL DIABETES

REFERENCE TO RELATED APPLICATIONS

This application is a continuation of U.S. patent application Ser. No. 10/441,992 filed on May 20, 2003, which is a continuation-in-part of U.S. patent application Ser. No. 10/317,916 filed Dec. 12, 2002. The disclosures of each of the foregoing are incorporated herein by reference in their entirety.

TECHNICAL FIELD

The present invention relates to methods for using human placental alkaline phosphatase, an enzyme produced by human placenta during pregnancy, to reduce blood glucose level in a mammal. Treatment regimens provided by the invention may be used to control Type 1 and Type 2 forms of diabetes in humans.

Significant recent changes in human behavior and lifestyle as well as the human environment have resulted in the escalation of diabetes during the last decades. Diabetes is a disease characterized by elevated levels of blood plasma glucose, or hyperglycemia. Hyperglycemia, if uncontrolled, can lead to other complications, such as blindness, kidney disease, heart disease, stroke, nerve diseases, circulatory disorders, and impotence in males. Diabetes is a chronic disease with diverse pathologic manifestations, and is accompanied by lipid metabolism and cardiovascular disorders as well as glycometbolism disorders.

Diabetes mellitus is a hetergeneous group of disorders characterized by high blood glucose (sugar) levels. There are two main types of diabetes. Type 1, or insulin dependent diabetes, results from a deficiency of insulin due to autoimminunological destruction of the insulin-producing pancreatic β-cell islets [Bell, G. I. and Polonsky, K. S., "Diabetes mellitus and genetically programmed defects in β-cell function." *Nature* 414, 788-791(2001); Mathis, D., Vence, L. and Benoist, C., "β-cell death during progression to diabetes." *Nature* 414, 792-798(2001)]. People with Type 1 diabetes must take exogenous insulin for survival to prevent the development of ketoacidosis.

In Type 2 diabetes, or non-insulin-dependent diabetes mellitus (NIDDM), muscle, fat, and liver cells are resistant to the actions of insulin. Furthermore, compensatory mechanisms that are activated in β-cells to secrete more insulin to maintain blood glucose levels within a normal physiological range fail to function properly. Type 2 diabetes accounts for about 90% of all diabetes [Saltiel, A. R., "New perspectives into the molecular pathogenesis and treatment of Type 2 diabetes." *Cell* 104, 517-529 (2001)]. Type 2 diabetics are often prescribed blood glucose-lowering sulfonylurea-based or -derived drugs, which are associated with the stimulation of insulin production in the pancreatic β-cells. Alternatively, patients sufferng from Type 2 diabetes may also be prescribed biguanide-based or -derived drugs, which are associated with increasing a patient's sensitivity to insulin.

Diabetes already afflicts an estimated 6% of the adult population in Western society, and its worldwide frequency is projected to grow by 6% per annum, potentially reaching a total of 200-300 million cases in 2010 [Zimmet P., Alberti, K. G. M. and Shaw, J., "Global and societal implications of the diabetes epidemic." *Nature* 414, 782-787 (2001)]. The main forces driving this increasing incidence are sedentary lifestyle and a staggering increase in obesity.

Diabetes is a potentially very dangerous disease because it is associated with markedly increased incidence of coronary, cerebral, and peripheral artery disease. As a result, patients with diabetes have a much higher risk of myocardial infarction, stroke, limb amputation, renal failure, or blindness. Atherosclerotic cardiovascular disease is responsible for 80% of diabetic mortality and more than 75% of all hospitalizations for diabetic complications [Moller, D. E., "New drug targets for Type 2 diabetes and the metabolic syndrome." *Nature* 414, 821-827 (2001)]. Recent evidence indicate that hyperglycemia leads to overproduction of superoxide accounting for vascular damage, which, in turn, underlies most diabetic complications [Brownlee, M., "Biochemistry and molecular cell biology of diabetic complications." *Nature* 414, 813-820 (2001); Ho, E. and Bray, T. M., "Antioxidants, NFκB activation, and diabetogenesis." *Proc. Soc. Exp. Biol. Med.* 222, 205-213 (1999)].

Despite large variations in carbohydrate intake with various meals, blood glucose normally remains in a narrow range between 4 and 7 mM in non-diabetic individuals. Such tight control is regulated by the balance among three major mechanisms, i.e. (i) glucose absorption from the intestine, (ii) glucose production by the liver, and (iii) uptake and metabolism of glucose by the peripheral tissues, mainly the skeletal muscle and fat tissue. In skeletal muscle and fat tissue, insulin increases the uptake of glucose, increases the conversion of glucose to glycogen, and increases conversion of glucose to fat (mainly triglycerides). In the liver, insulin inhibits the release of glucose from glycogen. Insulin is the only known hormone which can regulate all three mechanisms required to maintain the blood glucose level in the normal range [Saltiel, A. R. and Kahn, C. R., "Insulin signaling and the regulation of glucose and lipid metabolism." *Nature* 414, 799-806 (2001)].

At present, the only established available treatment for severe Type 1 diabetes is daily (often multiple) insulin injection. Apart from the inconvenience of the injection procedure, several adverse effects may accompany insulin treatment, including occasionally severe hypoglycemia (lower than normal blood glucose level) and weight gain; unfortunately, this latter side effect can make the target tissues even more resistant to the actions of insulin [U.K. Prospective Diabetes Study Group, "U.K Prospective Diabetes Study 16. Overview of 6 years' therapy of Type 2 diabetes: A progressive disease." *Diabetes* 44, 1249-1258 (1995)]. On an experimental basis, clinical islet transplantation is also gaining acceptance, particularly for patients with hypoglycemic awareness [Ryan, E. A., Lakey, J. R. T., Paty, B. W., Imes, S., Korbutt, G. S., Kneteman, N. M, Bigam, D., Rajotte, R. V. and Shapiro, A. M. J., "Successful islet transplantation: Continued insulin reserve provides long-term glycemic control." *Diabetes* 51, 2148-2157 (2002)]; however, this method is still far from established. Apart from the problem that it is very difficult to adjust insulin production to meet the patient's needs, immuno-suppressants, which are used to prevent rejection of the transplanted tissue, can exert potent and undesirable side effects. It is obvious that even partial replacement of insulin with a safer and effective agent that does not require a complicated surgical procedure would greatly benefit Type 1 diabetic patients.

In Type 2 diabetes, an aggressive control of hyperglycemia by medication is essential; otherwise this disease will progress into the even more dangerous Type 1 diabetes. Several drugs in five major categories, each acting by a different mechanism, are available for this purpose [Moller, D. E., "New drug targets for Type 2 diabetes and the metabolic syndrome." *Nature* 414, 821-827 (2001)]:

(A) Insulin secretogogues, including sulphonylureas (e.g., glipizide, glimepiride, glyburide) and meglitinides (e.g., nateglidine and repagnnide), enhance secretion of insulin by acting on the pancreatic β-cells. While this therapy can decrease blood glucose level, it has limited efficacy and tolerability. In addition, it causes weight gain and often induces hypoglycemia. Finally, patients often become refractory to this treatment.

(B) Biguanides (e.g., metformin) are thought to act primarily by decreasing glucose production in the liver. Biguanides often cause gastrointestinal disturbances and lactic acidosis, which limits their use.

(C) Inhibitors of α-glucosidase (e.g., acarbose) decrease absorption of glucose from the intestine. These agents also often cause gastrointestinal disturbances.

(D) Thiazolidinediones (e.g., pioglitazone, rosiglitazone) act on a specific receptor (peroxisome proliferator-activated receptor-gamma (PPARγ)) in the liver, muscle and fat tissues. They regulate lipid metabolism and thus enhance the response of these tissues to the actions of insulin. Frequent use of these drugs may lead to weight gain and may induce edema and anemia.

(E) Insulin is used in more severe cases, either alone or in combination with the above agents.

All these medications are given to the patient daily, often two or three times a day.

Because each agent that is being used in the medical treatment of diabetes has either significant side effects or causes weight gain (which, in turn, further impairs the actions of insulin), or both, newer approaches to control Type 2 diabetes are desperately needed. An effective new treatment would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent (e.g., once per week) usage; and (e) it would be usable in combination with tolerable amounts of any of the categories of drugs listed above.

Placental alkaline phosphatase (PALP) is a member of the alkaline phosphatase group of enzymes that hydrolyze phosphate-containing compounds at alkaline pH. Mature PALP is a dimer of two identical glycosylated subunits. A primary source of PALP is human placenta, which synthesizes this enzyme during pregnancy so that toward the end of third term the enzyme's level in the placenta tissue and maternal/fetal blood becomes very high. Therefore, it is very unlikely that human PALP exerts toxic or pathological effects in human tissues. Subunits of human placental alkaline phosphatase have an approximate molecular weight of 66 kDa, as determined by gel electrophoresis.

A determination of an in vivo half-life for human PALP was reported in 1965 [Clubb, J. S., Neale, F. C. and Posen, S., "The behavior of infused human placental alkaline phosphatase in human subjects." *J. Lab. & Clin. Med.* 66, 493-507 (1965)]. In human subjects, injected PALP is reported to remain remarkably stable in the circulation, with an estimated biological half-life of about 7 days. In the reported experiments, PALP was injected as a minor constituent in a mixture of PALP and albumin obtained by extraction, without further purification. The authors reported that PALP up to serum concentration of 975 "King-Armstrong" (KA) units appeared metabolically inert, and hypothesized that PALP performs no measurable physiological function in circulation.

The physiological function of PALP has been unknown until recently, when Kiss and his co-workers discovered that, in human fetus and mouse embryo fibroblasts, the enzyme functions both as a growth factor and a promoter of survival in serum factor-deficient culture medium [She, Q.-B., Mukherjee, J. J., Huang, J.-S., Crilly, K. S. and Kiss, Z., "Growth factor-like effects of placental alkaline phosphatase in human and mouse embryo fibroblasts." *FEBS Lett.* 469, 163-167 (2000); She, Q.-B., Mukherjee, J. J., Chung, T. and Kiss, Z., "Placental alkaline phosphatase, insulin, and adenine nucleotides or adenosine synergistically promote long-term survival of serum-starved mouse embryo and human fetus fibroblasts." *Cellular Signalling* 12, 659–665 (2000)].

SUMMARY OF THE INVENTION

In one embodiment, the present invention provides a method of reducing blood glucose level in a mammal, comprising the step of administering a therapeutically effective amount of purified human placental alkaline phosphatase, or an active derivative. The mammal may be a human. The method may be effective to reduce a human's blood glucose level to below about 10 mM, and preferably into the normal range of 4 mM to 7 mM. The method may be used on a diabetic human, and may be used in combination with administration of an anti-diabetic medicament.

In another embodiment, the invention provides a treatment regimen for treating diabetes, comprising periodic administration to a diabetic human of a therapeutically effective amount of purified human placental alkaline phosphatase, or an active derivative. The treatment regimen may be used in combination with administration of an anti-diabetic medicament. The treatment regimen may be effective to maintain the human's blood glucose level below about 10 mM, and preferably within the normal range of 4 mM to 7 mM.

In another embodiment, the invention provides a preparation for administration to a human, the preparation comprising homogeneous purified human placental alkaline phosphatase in a physiologically acceptable carrier.

DETAILED DESCRIPTION OF THE INVENTION

Figure 1:
FIG. 1 shows a picture of a gel separation, demonstrating that homogeneous purified PALP used for the experiments described in Examples 21, 22, and 24 does not contain any contaminating protein.

The observation of the statutory effects of PALP on cell proliferation, described above, led to the experiments described in the Examples herein. In a first set of experiments, the effects of PALP on blood glucose level were determined by glucose tolerance tests in mice, as well as in models for Type 1 and Type 2 diabetes. In a second set of experiments, the effects of PALP on cellular glucose uptake in appropriate model systems for fat tissue (differentiated L1 adipocyces) and skeletal muscle (differentiated L6 muscle cells) were observed.

The results of the sets of experiments demonstrate that PALP has powerful insulin-independent stimulatory effects on glucose uptake and metabolism in vitro and corresponding significant glucose lowering effects in vivo, without pathological effects and without causing weight gain. The data, combined with other observations including a) that high levels of PALP appear to covert only positive physiological effects in pregnant women, and b) that the enzyme is very stable in the circulation, indicate that PALP is likely to provide effective, safe, and sustained control of hyperglycemia in diabetic patients. Accordingly, the invention includes the use of PALP as an effective and safe blood glucose-reducing agent, and as an effective agent in a treatment regimen for the treatment of diabetes.

Method for Reducing Blood Glucose Level

In one embodiment, the present invention provides a method of reducing blood glucose level in a mammal, comprising the step of administering a therapeutically effective amount of purified human placental alkaline phosphatase, or an active derivative. The term "therapeutically effective amount" in this specification and in the claims indcates a dosage that is effective in, or is targeted to, either attaining a desired level of blood glucose or maintaining a desired level of blood glucose over an appropriate time window.

In the practice of the methods of this embodiment, the mammal may be a human. The method may be effective to reduce a human's blood glucose level to below about 10 mM, and preferably into the normal range of about 4 mM to about 7 mM. The method may be used on a diabetic human, and may be used in combination with administration of an anti-diabetic medicament.

The method may also be used for preventing the onset of Type 2 diabetes, for a human that is at risk for the development of diabetes. In particular, the method may be appropriate for a human that exhibits a chronically elevated blood glucose level but that has not yet been diagnosed with diabetes. Furthermore, the method may be useful for preventing a progression from Type 2 diabetes to Type 1 diabetes. This is because the persistently high blood glucose levels associated with Type 2 diabetes eventually leads to the destruction of insulin-producing β-cells in the islets of Langerhans, resulting in an insulin deficiency.

The Active Component

The active component in the methods and compositions of the present invention is human PALP, or an active derivative thereof. As used herein, the term "PALP" and the phrase "human PALP" are used interchangebly to refer to human placental alkaline phosphatase.

As is demonstrated by the example herein, whole PALP enzyme in its native state is not required to achieve a glucose-reducing effect. Active derivatives of PALP are therefore suitable for the practice of the present invention. For example, digestion of PALP by a protease, such as bromelain, may provide an active derivative. Likewise, one who is skilled in the art may synthesize or develop an active derivative that is a smaller fragment of a PALP sequence which demonstrates efficacy similar to that of native PALP enzyme. By way of example, modification of a PALP sequence, or a sequence of smaller PALP peptides, by exchanging amino acids at critical sites to yield an active derivative may improve the glucose-reducing effect disclosed herein. In the practice of the present invention, it is envisioned that modified PALP, smaller PALP-derived peptides, or modified PALP-derived peptides may be similarly effective or even more effective than the native PALP enzyme, and are each considered to be active derivatives.

Human PALP in solid form is available commercially from Sigma Chemical (St Louis, Mo.), for example (Sigma catalog number P3895; CAS Registry Number 9001-78-9). Another commercial source of human PALP is Calbiochem (San Diego, Calif.; catalog number 524604).

Human PALP may also be obtained by extraction from placental tissue. For example, a partially purified preparation may be obtained by butanol extraction of homogenized placenta Other methods of extraction from placental tissue are also suitable.

Human PALP, or an active derivative, may also be obtained by chemical synthesis using conventional methods. For example, solid phase synthesis techniques may be used to obtain PALP or an active derivative. Recombinant methods of obtaining quantities of PALP are also suitable, as is known in the art.

The methods and treatment regimens described herein include administration of purified human placental alkaline phosphatase, or an active derivative. In the practice of the present invention, PALP or an active derivative is generally administered in the form of a preparation comprising the PALP enzyme or active derivative. The term "preparation" as used herein means a composition comprising purified human PALP or active derivative dissolved or dispersed in a carrier. In a preparation for administration to a human, the carrier should be a physiologically acceptable carrier.

The term "purified" is used herein to encompass compositions that are obtained from a starting material by one or more purification steps (such as solvent extraction, column separation, chromatographic separation, etc.) that enhance the concentration of active agent relative to the starting material. The term "purified" also encompasses compositions that contain a significant quantity of active agent in relation to impurities, whether obtained by a purification process or not. The term "purified" should not be construed to connote absolute purity.

The phrase "purified human placental alkaline phosphatase" therefore includes compositions such as a partially purified human PALP available from Sigma Chemical, which was used as a starting material for the experiments described in the following Examples.

A purified human PALP composition may also be obtained, for example, by a purification procedure described elsewhere [She, Q.-B., Mukherjee, J. J., Huang, J.-S., Crilly, K. S. and Kiss, Z., "Growth factor-like effects of placental alkaline phosphatase in human and mouse embryo fibroblasts." *FEBS Lett.* 469, 163-167 (2000)].

The term "homogeneous" is used herein to indicate a composition that yields a single protein band in an electrophoretic gel separation, such as by the SDS-PAGE technique described in Example 1. The phrase "homogeneous purified human placental alkaline phosphatase" therefore includes compositions that yield a single band for PALP enzyme in an electrophoretic separation. A homogeneous purified human PALP may be obtained, for example, by the purification procedures described in Example 1.

A separate consideration is the degree of purity that is required for PALP material that is to be used in a preparation for administration to a human. An advantage of using a preparation comprising highly purified or homogeneous PALP in the methods and treatment regimens of the present invention is that possible side effects caused by contaminating proteins will not be an issue. However, less extensively purified PALP preparations, such as that comprising the commercially available human PALP from Sigma, may also be used so long as safety can be demonstrated. Since each additional purification step results in significant loss of the enzyme, using less purified PALP material for PALP preparations wold be more cost-effective.

Administration of PALP

Since human PALP is a relatively large protein, and its actions appear to involve the adipose tissue and muscle, systemic administration is an appropriate mode of administration.

By way of example, systemic administration may include administration of a PALP-containing preparation. For administration to a human, purified human PALP is dissolved or dispersed in physiological saline or in another physiologically acceptable carrier, or enclosed in liposomes such as immunoliposomes, or other delivery systems or formulations as are known to the art, to produce a PALP-containing preparation.

For example, one suitable PALP preparation for the practice of the present invention comprises purified human PALP dissolved in a 0.9 N physiological sat solution to yield a PALP concentration of 10 mg/mL. Another suitable PALP preparation comprises purified human PALP dissolved in a 0.9 N physiological salt solution to yield a PALP concentration of 30 mg/mL.

A PALP preparation may be administered by injection, for example. A PALP preparation may be administered via intravenous injection, intraperitoneal injection, subcutaneous injection, intradermal injection, intramuscular injection, or any other mode of delivery that ensures appropriate distribution and relative stability of the enzyme in the body.

In one embodiment of the method, purified human placental alkaline phosphatase, or an active derivative, is administered to a human. A common way to express a suitable dosage is grams of active agent per square meter of body surface area for the subject. Several formulas are known for estimating a human subject's body surface area, based on the human's height (in cm) and mass (in kg). Table 1 lists a variety of known formulas for estimating body surface area (BSA) proposed by researchers. Other suitable formulas may likewise be employed.

TABLE 1

Formulas for estimating body surface area (BSA).

| Author(s) | BSA formula |
|---|---|
| Du Bois and Du Bois | BSA (m$^2$) = Mass(kg)$^{0.425}$ × Height(cm)$^{0.725}$ × 0.007184 |
| Gehan and George | BSA (m$^2$) = Mass(kg)$^{0.51456}$ × Height(cm)$^{0.42246}$ × 0.02350 |
| Haycock | BSA (m$^2$) = Mass(kg)$^{0.5378}$ × Height(cm)$^{0.3964}$ × 0.024265 |
| Mosteller | BSA (m$^2$) = Mass(kg)$^{0.5}$ × Height(cm)$^{0.5}$ × 0.016666 |

Preferably, a dosage of about 0.2 to about 3 g/m$^2$ of purified human PALP or active derivative is administered to the human; more preferably, a dosage of about 0.2 to about 1.0 g/m$^2$ is administered to the human.

The human may have an elevated blood glucose level before administration of purified human PALP. By "elevated," it is meant that the human's blood glucose level is greater than the normal range of about 4 to about 7 mM.

Systemic administration of PALP preferably reduces blood glucose level in a human to below about 10 mM, more preferably to below about 8 mM, and most preferably to within the normal range of about 4 to about 7 mM.

Because of the relatively large size of the PALP enzyme, its partition into target tissues after administration is expected to be slow. Preferably, PALP is administered several hours prior to an expected glucose load; more preferably PALP is administered at least about 12 hours prior to the expected glucose load; most preferably, PALP is administered at least about 24 hours prior to the expected glucose load.

In another embodiment of the method, purified human PALP, or an active derivative, is administered to a diabetic human. The diabetic human may be afflicted with either Type 1 or Type 2 diabetes.

In the treatment of a diabetic human, administration of purified human PALP may be used in combination with insulin or any anti-diabetic medicament (i.e. biguanides, insulin secretogogues such as sulphonylureas or meglitinides, inhibitors of α-glucosidase, thiazolidinediones, and others). In this embodiment, the anti-diabetic medicament is administered as part of a planned course of treatment for diabetes, in conjunction with purified human PALP. The anti-diabetic medicament may be administered orally or by any other conventional method. While some diabetic medicaments may work in combination with PALP more effectively than others, presently no contra-indication for using any medicament in combination with PALP has been observed.

For fine-tuning of glucose level in PALP-treated diabetic patients, a recently developed long-acting derivative of glucagon-like peptide-1 (GLP-1), NN2211, may be especially useful as the anti-diabetic medicament. NN2211 has the useful property that it enhances insulin secretion by the islet only at higher than normal blood glucose levels [Rolin, B., Larsen, M. O., Gotfredsen, C. F., Deacon, C. F., Carr, R. D., Wilken, M. and Knudsen, L. B., "The long-acting GLP-1 derivative NN2211 ameliorates glycemia and increases β-cell mass in diabetic mice." *Am. J. Physiol. Endocrinol. Metab.* 283, E745-E752 (2002)].

In the combination of treatments, the patient's situation will determine if the administration of PALP occurs prior to or after administration of the anti-diabetic medicament. For example, if glycemic control is required very rapidly, then insulin will be administered first followed by administration of PALP; in this embodiment administration of PALP will ensure long-lasting glycemic control.

Treatment Regimen for Treating Diabetes

In another embodiment, the invention provides a treatment regimen for treating diabetes, comprising periodically administering to a diabetic human a therapeutically effective amount of purified human placental alkaline phosphatase, or an active derivative. The method may be used in combination with administration of an anti-diabetic medicament. The method may be effective to maintain the human's blood glucose level below about 10 mM, and preferably in the normal range of 4 mM to 7 mM.

The treatment regimen employs the same active component, purified human placental alkline phosphatase or active derivative, described above. The active component may be obtained and purified as described above.

Administration of purified human PALP in the treatment regimen may also be carried out as described above. PALP preparations described herein are also suitable for use in the treatment regimens.

As used with respect to the treatment regimens described herein, the term "periodically" refers to repeated administration of purified human PALP targeted to maintaining blood glucose level within a desired range over the time of treatment. The term "periodically" includes repeated administration at fixed intervals, but also includes repeated administration over irregular intervals as is required by the patient's condition. Furthermore, in the treatment regimens of this embodiment, the therapeutically effective amount of purified human PALP that is administered does not need to be identical for each separate administration. More or less purified human PALP may be administered in separate administrations, as the patient's needs dictate.

As will be appreciated by those skilled in the art, the dosage and the number of treatments will be dependent on the severity of diabetes and the tolerance of the individual patient. Preferably, about 0.2 to about 3 g/m$^2$ is administered to the patient once daily; more preferably, about 0.2 to about 1.0 g/m$^2$ is administered to the patient once daily; even more preferably, about 0.2 to about 3 g/m$^2$ is administered to the patient once or twice weekly; and most preferably about 0.2 to about 3 g/m$^2$ is administered to the patient once biweekly.

It is expected that in severe cases of both Type 1 and Type 2 diabetes, once weedy, twice weekly, or daily administration of PALP or active derivative will result in significant reduction of blood glucose level. The treatment regimen may be effective to maintain the human's blood glucose level below about 10 mM, preferably below about 8 mM, and most preferably in the normal range of 4 mM to 7 mM.

Furthermore, administration of an anti-diabetic medicament in combination with the PALP may help to fully normalize glucose levels. In the treatment regimens of this embodiment, administration of purified human PALP may be used in combination with insulin or any anti-diabetic medicament (i.e. biguanides, insulin secretogogues such as sulphonylureas or meglitinides, inhibitors of α-glucosidase, thiazolidinediones, and others) to ensure fine-tuning of glycemic control as required. The anti-diabetic medicament may be administered orally or by any other conventional method. A recently developed long-acting derivative of glucagon-like peptide-1 (GLP-1), NN2211, may be especially useful. While some of the anti-diabetic medicaments may work in combination with PALP more effectively than others, presently no contra-indication for using any medicament in combination with PALP has been observed.

By treating a diabetic patient using the treatment regimens described herein, control over diabetes-related conditions may be attained. For example, treatment by the treatment regimens may be effective to reduce diabetes-associated weight loss for a patient that would normally experience weight loss when treated by an alternative method. Furthermore, the treatment regimens may be effective in treating other diabetes-related complications that have been linked to hyperglycemia. Diabetes-related complications related to hyperglycemia include blindness, renal failure, and various neuropathies [Brownlee, M., "Biochemistry and molecular cell biology of diabetic complications." *Nature* 414, 813 (2001)].

Method for Inducing Weight Loss or Reducing Weight Gain

Another embodiment of the invention provides a method for treating a human to induce weight loss or to reduce weight gain, comprising regularly administering purified human placental alkaline phosphatase, or an active derivative, to the human in an effective amount to induce weight loss, to reduce an expected weight gain, or to maintain a constant body weight for the human over time.

The method may be particularly suitable for treatment of a human afflicted with Type 2 diabetes mellitus. The method may then be effective to induce weight loss or to reduce an expected weight gain preceding, caused by, or associated with diabetes.

The method may also be suitable to treat an obese person, whose blood glucose level is not elevated, to induce weight loss. Furthermore, the method may be suitable to treat a human who is obese and non-diabetic, but who has a chronically elevated blood glucose level prior to beginning treatment. In this embodiment, the treatment may be effective in preventing the onset of diabetes.

As used herein, the term "obese" refers to a condition where a person's body mass index (BMI) is about 30 kg/m$^2$ or greater. Body mass index is defined as a person's mass (in kilograms) divided by the square of the person's height (in meters). Persons who are in the obese category are known to be at greater risk for developing increased blood glucose (or "impaired glucose tolerance"), insulin insensitivity, and eventually Type 2 diabetes.

The method furthermore may be useful to induce weight loss or reduce an expected weight gain preceding the onset of diabetes for a person at risk for Type 2 diabetes. In this embodiment, the treatment may be effective in preventing the onset of diabetes.

The method employs the same active component, purified human placental alkaline phosphatase or active derivative, described above. The active component may be obtained and purified as described above.

Administration of purified human PALP in the method may also be carried out as described above. By way of example only, the step of administering may be performed by injection of a preparation comprising a physiologically acceptable carrier and human placental alkaline phosphatase or active derivative, dissolved or dispersed in the carrier. The mode of injection may be intravenous, subcutaneous, intraperitoneal, intramuscular, or intradermal.

PALP preparations described herein are suitable for use in the methods. By way of ample, one suitable preparation comprises homogeneous purified human placental alkaline phosphatase.

As used with respect to the methods described herein, the phrase "regularly administering" refers to repeated administration of purified human PALP targeted to induce weight loss or reduce an expected weight gain over the time of t =t- The expected weight gain may be caused by or associated with the onset of diabetes, for example. The term "regularly" includes repeated administration at fixed intervals, but also includes repeated administration over irregular intervals. Furthermore, in the methods of this embodiment, the effective amount of purified human PALP that is administered does not need to be identical for each separate administration. More or less purified human PALP may be administered in separate administrations, as the patient's needs dictate.

The step of regular administration may include administration of human placental alkaline phosphatase or active derivative about once per two week in some embodiments. In other embodiments, the step of regular administration may include administration of human placental alkaline phosphatase or active derivative about once per week, about twice per week, or even about once per day.

By way of example only, the effective amount may be in the range of about 0.2 grams to about 3 grams per square meter of calculated surface area for the human. In one embodiment, the effective amount is in the range of about 0.2 grams to about 1 gram per square meter of calculated surface area for the human. In another embodiment, the effective amount is in the range of about 1 gram to about 3 grams per square meter of calculated surface area for the human.

Physiologically Acceptable Preparation of Homogeneous PALP

In another embodiment, the invention provides a preparation for administration to a human, the preparation comprising homogeneous purified human PALP in a physiologically acceptable carrier. Human PALP may be obtained as described above, and may be purified to homogeneity by the purification procedures described in Example 1. By way of example, the preparation may be a PALP-containing solution in which homogeneous purified human PALP is dissolved or dispersed in physiological saline. Alternatively, the preparation may comprise homogeneous purified human PALP dissolved or dispersed in another physiologically acceptable carrier, or enclosed in liposomes such as immunoliposomes, or other delivery systems or formulations as are known to the art.

For example, one suitable preparation comprises homogeneous purified human PALP dissolved in a 0.9 N physiological salt solution to yield a PALP concentration of 10 mg/mL. Another suitable PALP preparation comprises homogeneous purified human PALP dissolved in a 0.9 N physiological salt solution to yield a PALP concentration of 30 mg/mL.

EXAMPLES

Example 1

Purification and Spectrophotometric Assay of PALP

Human PALP (Type XXIV, 1020 units of total activity) in a partially purified form was obtained commercially from Sigma Chemical. A butanol extraction of placental tissue, followed by one or more chromatographic steps, was performed by Sigma Chemical to obtain the partially purified material. Butanol extraction inactivates most of the other placental proteins, including growth factors, but does not reduce either the mitogenic or the enzymatic activity of PALP.

As determined by sodium dodecyl sulfate-polyacrylamide gel electrophoresis (SDS-PAGE), the partially purified PALP obtained from Sigma ("commercial PALP") was not homogeneous and contained other proteins. FIG. 1 shows a picture of a gel separation of a preparation comprising commercial PALP without further purification, and other preparations of PALP of increasing purity. Lane 2 represents a preparation comprising commercial PALP, lanes 3 and 4 represent preparations comprising commercial PALP material after further purification steps (described below), and lane 5 represents a preparation of homogeneous purified PALP obtained by the complete purification procedure described below. Lane 1 contains various molecular mass standards for comparison.

As can be seen by reference to FIG. 1 at lane 2, the preparation comprising commercial PALP contained proteins other than PALP, and did not yield a homogeneous band in the electrophoretic separation. The preparation comprising commercial PALP contains at least three major proteins (one is PALP at approximately 66 kDa, while a band at approximately 52 kDa is $\alpha_1$-antitrypsin) and several minor proteins. Referring to lane 5 of FIG. 1, the preparation comprising homogeneous purified PALP (obtained by the complete purification procedure described below) apparently contains only PALP.

A purification procedure consisting of several steps was performed to further purify the commercially obtained PALP and to yield a homogeneous band in electrophoretic separation The same purification procedure was followed that is described elsewhere [She, Q.-B., Mukherjee, J. J., Huang, J.-S., Crilly, K. S. and Kiss, Z., "Growth factor-like effects of placental alkaline phosphatase in human and mouse embryo fibroblasts." *FEBS Lett.* 469, 163-167 (2000)].

A preparation of partially purified PALP was prepared by dissolving 350 mg of commercial PALP into 10 mL of buffer A (0.1 M sodium acetate, 0.5 M NaCl, 1 mM $MgCl_2$, 1 mM $CaCl_2$, adjusted to pH 6.5). This preparation was then further purified by successive Concanavalin A-Sepharose and Q-Sepharose chromatography, essentially following the procedure described elsewhere [Chang, T.-C; Huang, S.-M, Huang, T.-E and Chang, G.-G., "Human placenta alkaline phosphatase: An improved purification procedure and kinetic studies." *Eur. J. Biochem* 209, 241-247 (1992)], as follows.

The preparation was run through a Concanavalin A-Sepharose column using buffer A as solvent. For elution, buffer A included 50 mM α-methyl-D-mannopyranoside. Active fractions collected from the effluent were pooled and dialyzed against buffer B (50 mM Tris-HCl at pH 7.7). SDS-PAGE separation of the collected and dialyzed fraction is shown in FIG. 1 at lane 3.

The collected and dialyzed fraction from the previous step was then passed though a Q-Sepharose column. The fraction of interest was eluted with buffer B using a linear gradient of 0–250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 at lane 4, which demonstrates that at least two major proteins are still present in the fraction after dialysis.

Then, the collected and dialyzed fraction from the previous step was purified to homogeneity by t-butyl hydrophobic interaction chromatography (HIC). Prior to adding the fraction to a t-butyl HIC column the fraction was made 2 M in ammonium sulfate, and pH was adjusted to 6.8. The 5 mL bed volume t-butyl HIC cartridge (BIO-RADIATION, Hercules, Calif.) was connected to a fast performance liquid chromatography (FPLC) system from PHARMACIA (Peapack N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-0 M ammonium sulfate in 100 mM sodium phosphate at pH 6.8 was passed over the column. The negative linear gradient was used to elute a second protein-containing fraction, which contained the enzymatically active PALP protein.

The enzymatically active fraction from the HIC separation was dialed against phosphate-buffered saline and concentrated by Amicon ultrafiltration. Presence and purity of the PALP enzyme in the fraction was confirmed by SDS-PAGE. After electrophoretic separation, the gel was stained using coomassie blue or silver stain for visual observation of protein bands. A single protein band was observed with an approximate molecular weight of 66 kDa (FIG. 1, lane 5). Identification of the PALP band by sequence analysis was performed by the Mayo Clinic Protein Core Facility (Rochester, Minn.).

PALP enzyme activity was assayed spectrophotometrically by monitoring the hydrolysis of 4-nitrophenylhosphate (as an increase in absorbance at 410 nm) at room temperature (22° C.) as described elsewhere [Chang,-G.-G., Shiso, M.-S., Lee, K.-R and Wu, J.-J., "Modification of human placental alkaline phosphatase by periodate-oxidized 1,$N^6$-ethenoadenosine monophosphate." *Biochem J.* 272, 683-690 (1990)]. Activity analysis of 5-10 μg purified enzyme was performed in 1 mL incubation volume containing 50 mM $Na_2CO_3$/$NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 μmol substrate hydrolyzed/min at 22° C. at pH 9.8.

Examples 2-8

Effects of PALP on Blood Glucose Levels and Body Weight in Mice

Example 2

Determination of Blood Glucose Levels in Treated and Untreated Healthy Mice in Glucose Tolerance Tests Two preparations of commercial PALP, without further purification, were prepared. A first preparation included 30 mg/mL commercial PALP in a 0.9 N physiological salt solution. A second preparation included 10 mg/mL commercial PALP in a 0.9 N physiological salt solution.

First-generation hybrid BDF1 (C57B1/6 female×DBA/2 male) adult (10 to 12 weeks old) male mice, weighing 22-23 g each, were used in the experiment. These animals, developed in the National Cancer Institute (Budapest, Hungary), are in the specified pathogen-free (SPF) hygienic category. The subject animals were kept in macrolon cages at 22-24° C. and 50-60% humidity, with lighting regimen of 12 hours light/12 hours dark. The animals had free access to tap water and were fed a sterilized standard diet (Charles River VRF1, autoclavable; Germany) according to the provided instructions. The animals were cared for according to "Guiding Principles for the Care and Use of Animals" based upon the Helsinki Declaration.

The mice were fasted for 16 hours before administration of glucose. Four groups of mice were treated and observed in this experiment. A first group was treated by intraperitoneal injection of 500 μg commercial PALP (50 μL injection of the second preparation) exactly 16 hours prior to intraperitoneal administration of glucose (2 mg/mouse). A second group was treated by intraperitoneal injection of 1500 μg commercial PALP (50 μL injection of the first preparation) 24 hours prior to intraperitoneal administration of glucose (2 mg/mouse). A third group was treated by 0.5 I.U. insulin, 15 minutes prior to administration of glucose (2 mg/mouse). A control group received only intraperitoneal administration of glucose (2 mg/mouse).

Blood glucose concentration was monitored for mice of each group, over a period of six hours after administration of glucose. Blood samples were taken from the corner of the eyes (canthus), and glucose concentrations in whole blood samples were immediately measured with the fast Glucose C test (Wako Chemicals USA Inc., Richmond, Va.). Data is shown in the graph of FIG. 2.

Figure 2:
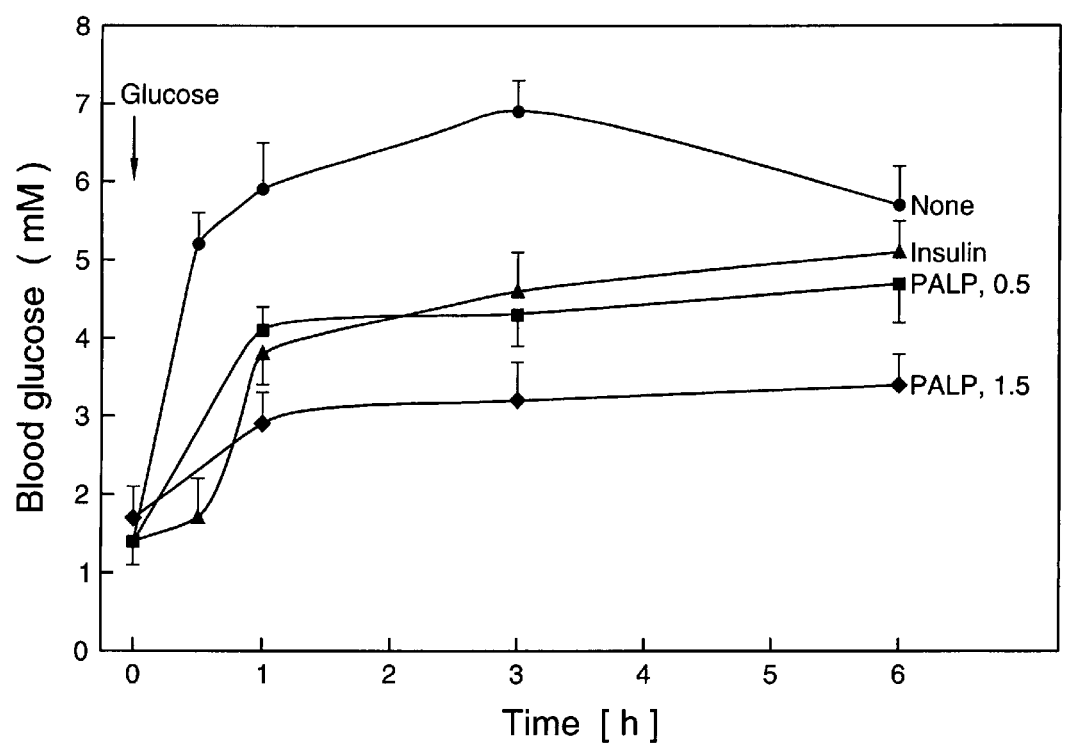
FIG. 2 demonstrates that in BDF1 male fasting mice, administration of a preparation comprising commercial PALP prior to a glucose load substantially reduced an increase in blood glucose level.

The data shown in FIG. 2 demonstrates that, for mice of the control group (●), glucose blood levels increased 3.2 to 4.3-fold within 0.5 to 6 hours after intraperitoneal glucose administration, with a maximum increase at the 3-hour time point. For mice receiving insulin treatment (▲), insulin was effective to initially (i.e., at 30 minutes) block a sharp increase in blood glucose level, but at later time points it was progressively less effective, and at the 6-hour time point it had no significant effect. For mice receiving 500 μg PALP (■), an effect was observed similar to that observed with insulin at the 1-, 3- and 5-hour time points. Finally, for mice receiving 1500 μg PALP (◆), the PALP treatment resulted in greater inhibitory effects on glucose levels than that was observed with insulin at the 1-, 3- and 6hour time points.

This glucose tolerance experiment clearly indicated that an appropriate amount of PALP may have longer-term effects than insulin when used at a concentration that is safe in animals. In other experiments (not shown), it was determined that for maximal effects PALP needs to be administered about 16 to about 24 hours prior to the glucose load. It is thought that preadministration is more effective because PALP is a relatively large molecule and its distribution in the body takes time. This observation is also an indication that PALP is metabolically stable in vivo. Indeed, others demonstrated that in human subjects injected PALP remains remarkably stable in the circulation with an estimated biological half-life time of 7 days [Clubb, J. S., Neale, F. C. and Posen, S., "The behavior of infused human placental alkaline phosphatase in human subjects." *J. Lab. & Clin. Med.* 66, 493-507 (1965)]. It is expected that, for the treatment regimens described herein, metabolic stability will allow administration of PALP once every 5-14 days, in contrast to practically all anti-diabetic drugs that are presently available, which require daily (often multiple) doses.

Example 3

PALP Decreases Blood Glucose Level in Streptozotocin-treated BDF1 Mice

BDF1 male mice, weighing 27-28 g each, were used. Four groups of mice were treated and observed in this experiment. A first group and a second group were initially treated by intraperitoneal injection of 1500 µg of commercial PALP (50 µL injection of the first preparation from Example 2). A third group and fourth group were untreated.

Twenty-four hours later (day 0), the first group and third group were treated once with streptozotocin (STZ) at a dosage of 200 mg/kg. STZ is widely used to selectively destroy insulin-producing β-cells in the islet by an oxidative mechanism. The second group and fourth group were untreated at this time. Mice in the first and second groups were then repeatedly administered 1500 µg commercial PALP by intraperitoneal injection (50 µL injection of the first preparation from Example 2) on days 2, 3, 4, and 5.

Blood glucose concentration was monitored for five mice of each group, over a period of six days after administration of STZ (day 0). Blood samples were taken from the eyes, and glucose concentrations in whole blood samples were immediately measured by the Glucose C test. Blood glucose concentration was determined on days 0, 3, 4, 5 and 6. Data is shown in the graph of FIG. 3

Figure 3:
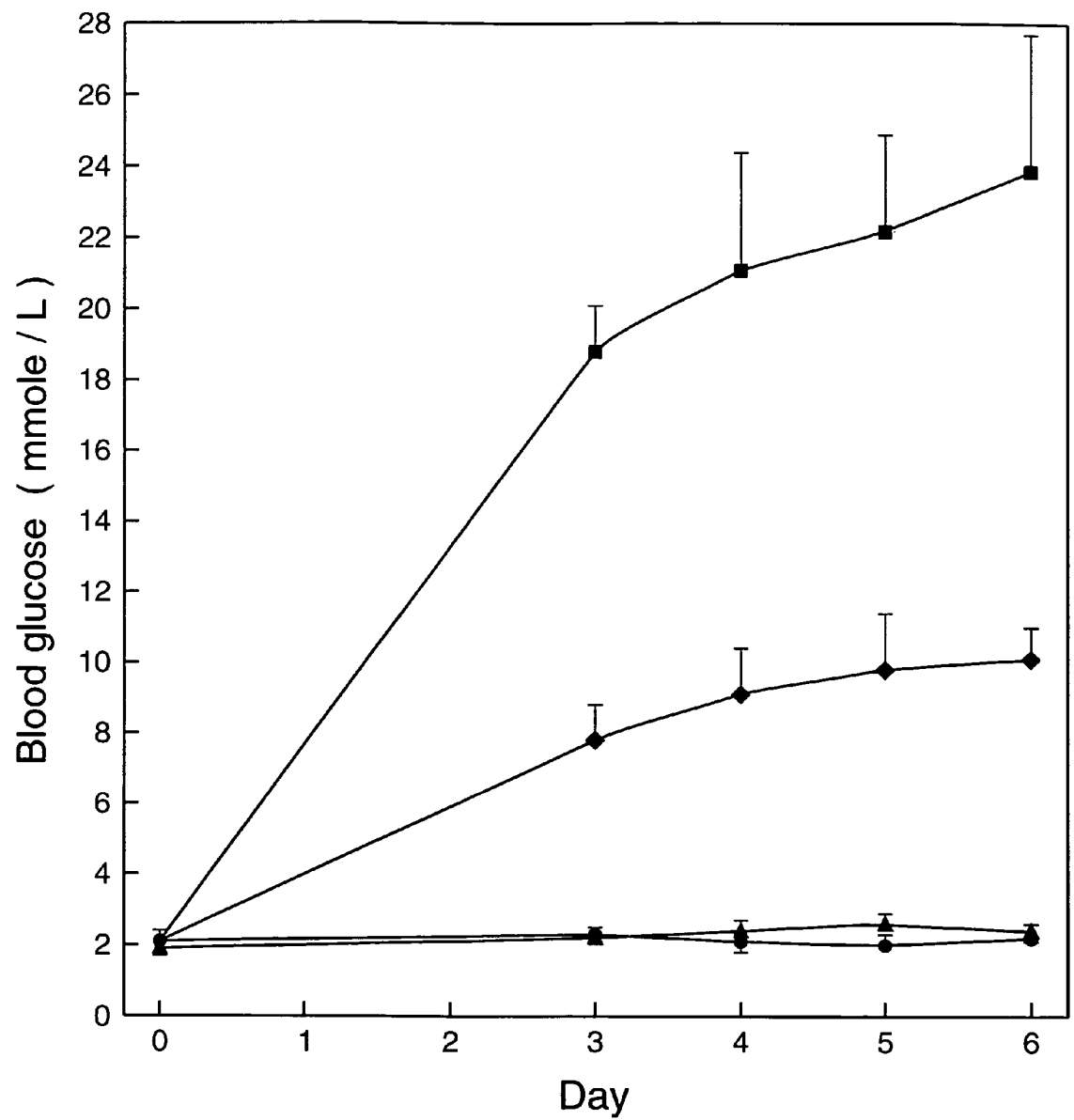
FIG. 3 demonstrates that in BDF1 male mice, intraperitoneal application of streptozotocin increased blood glucose level about 9-fold in three days(■), and that prior administration of a preparation comprising commercial PALP greatly reduced such increase in glucose level (♦).

The data shown in FIG. 3 demonstrates that, for mice of the fourth group (●) (untreated), the basal level of blood glucose was stable over the 6-day observation period. For mice of the second group (▲), administration of PALP did not increase, and, importantly, did not decrease the basal blood glucose level. For mice of the third group (■), treated with STZ in the absence of PALP, blood glucose level increased 9-fold by the third day and 10.9-fold by the sixth day. For the first group (♦), treatment with PALP decreased the effect of STZ by 63-67%.

These experiments clearly indicate that repeated administration of PALP is effective in reducing blood glucose levels for mice having damaged β-cells.

Example 4

PALP Decreases Blood Glucose Levels even After Pre-treatment with STZ

BDF1 male mice were initially treated with STZ (200 mg/kg). Two weeks after the initial treatments, the mice were treated with 1500 µg commercial-PALP (50 µL injection of the first preparation from Example 2) once daily for 5 days, and blood glucose was determined as before on the sixth day. PALP treatment reduced the average blood glucose level from 22.5 mM (n=5) for a control group to 11.5 mM (n=5) for the PALP-treated group.

This experiment strongly indicates that the effect of PALP on blood glucose levels is independent of insulin, because in STZ-treated animals practically no glycemic control remains (as shown by the ~10-times increase in glucose level compared to the fourth group of Example 3), which is consistent with the massive death of β-cells and the strong reduction or absence of insulin in the circulation. No attempt was made to determine the potentially greater effects of higher concentrations of PALP.

Example 5

Figure 4:
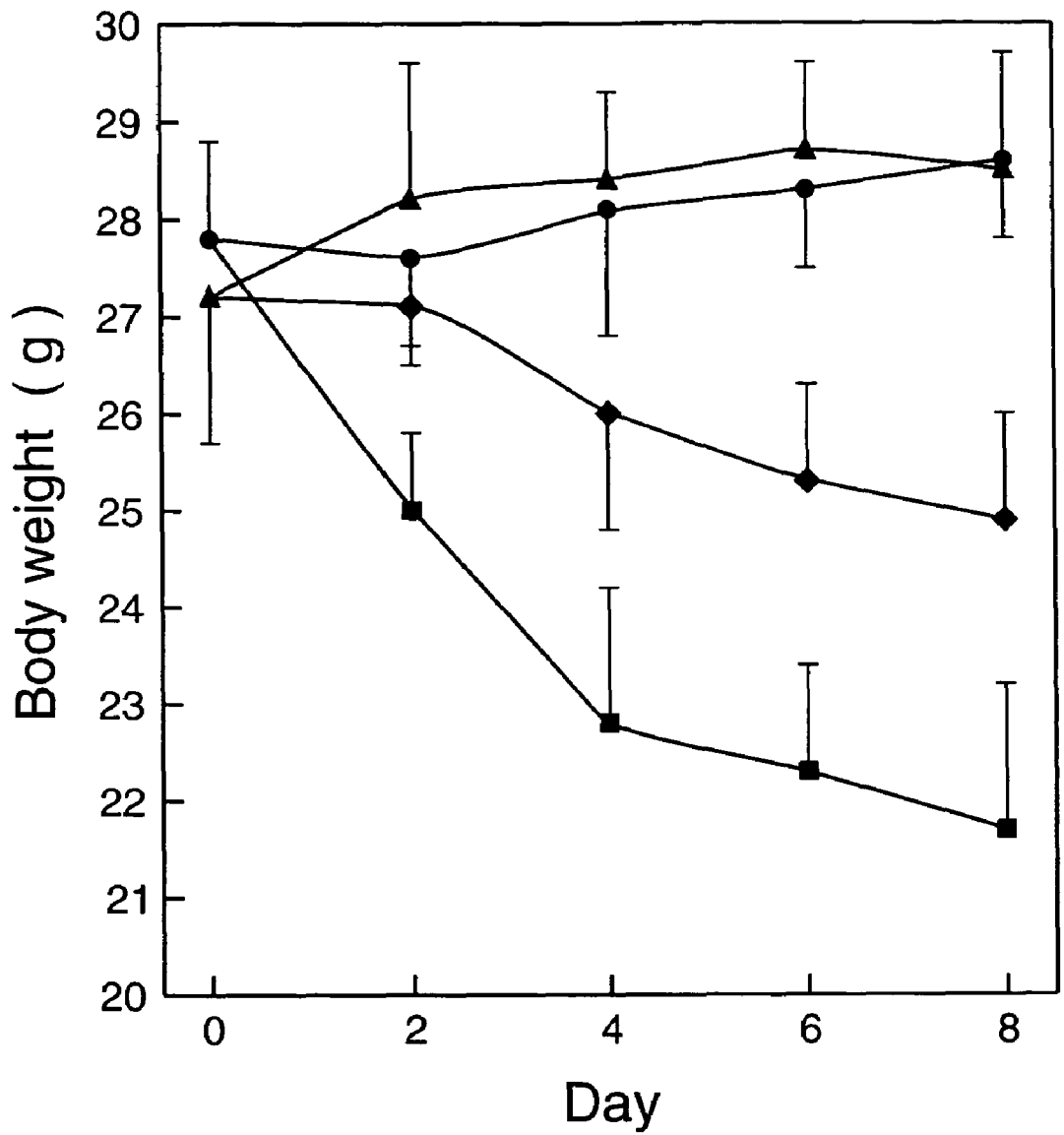
FIG. 4 demonstrates that in BDF1 male mice, intraperitoneal application of streptozotocin considerably decreased body weight over an eight day period (■), and that prior administration of a preparation comprising commercial PALP partially prevented the decrease in body weight (♦).

PALP Decreases the Loss of Body Weight Induced by Treatment with STZ, and Increases Life Span of STZ-treated Animals In the same experiment described in Example 3, the weight of each of the mice was measured on days 0, 2, 4, 6, and 8. Data is plotted in FIG. 4, which shows that mice from the untreated fourth group (●) and PALP-treated animals of the second group (▲) gained little, if any, weight during the 8-day observation period. Mice of the third group (■) treated with STZ in the absence of PALP lost approximately 5 grams. Weight loss for mice of the first group (♦) treated with both PALP and STZ was inhibited about 50%.

It is known that in the absence of insulin, protein degradation in muscles is enhanced leading to weight loss (wasting). In STZ-treated animals, this mechanism almost certainly plays a key role in weight loss. In unpublished work, Kiss and co-workers found that in differentiated L6 muscle cells, administration of PALP increases protein synthesis from various amino acids (alanine, proline, leucine, glutamine, methionine). Thus, stimulation of protein synthesis in muscle is likely to explain, at least in part, the ability of PALP to partially prevent weight loss in STZ-treated animals.

PALP, administered either subcutaneously or intraperitoneally, had a profound effect on the survival of STZ-treated animals. Of the 15 animals treated with STZ alone, only 6 survived up to 6 months. On the other hand, all 23 animals treated with STZ (one time) plus 1.5 mg PALP/mouse (for at least five consecutive days) survived for at least 8 months. Because conventionally a high survival rate of STZ-treated animals can be ensured only with daily injection of insulin, the positive effects of PALP on animal survival further indicate that PALP has insulin-like, but insulin-independent, physiological effects, including reduction of blood glucose level. Reduction in blood glucose level and increased protein synthesis together may explain the ability of PALP to promote survival of these animals.

Example 6

Determination of Blood Glucose Levels in Untreated and PALP-treated Non-obese Diabetic Mice In this set of experiments, the effect of PALP on blood glucose levels was determined in non-obese diabetic adult female mice. Data for the experiments is given in Table 2.

Non-obese (NOD) diabetic inbred adult (140-150 days old) female mice weighing 22-26 g each were obtained from Charles River Italia S.P.A. (Italy). The NOD mouse strain is a spontaneous animal model of human Type 1 diabetes isolated from the cataract-prone CTS subline of outbred ICR mouse. The mice are also in the specified pathogen-free (SPF) category. These mice are characterized by a cumulative incidence of diabetes, reaching 60-80% in females and 10-20% in males at an age of 150-200 days. In these mice, spontaneously autoreactive T-cells destroy the insulin-producing islet β-cells in the pancreas.

The following references provide a summary of the current understanding on how diabetes develops in NOD mice: Lyons, P. A., Armitage, N., Lord, G. J., Phillips, M. S., Todd, J. A., Peterson, L. B. and Wicker, L. S., "Mapping by Genetic Interaction: High resolution congenic mapping of the type 1 diabetes loci Idd10 and Idd18 in the NOD mouse." *Diabetes* 50, 2633-2637 (2002); Kaufman, D. J., Tish, R., Sarvetnick N., Chatenoud, L, Harrison, L. C., Haskins, K., Quinn, A., Sercarz, E., Herrath, M., Wegmann, D., Wen, L. and Zekzer, D., "Report from the 1$^{st}$ international NOD mouse T-cell workshop and the follow-up mini-workshop." *Diabetes* 50, 2459-2463 (2001); Bonifacio, E., Atkinson, M., Eisenbarth, G., Serreze, D., Kay, T. W. H., Lee-Chan, E. and Singh, B., "International Workshop on lessons from animal models for human type 1 diabetes: Identification of insulin but not glutamnic acid decarboxylase or IA-2 as specific autoantigens of humoral autoimmunity in nonobese diabetic mice." *Diabetes* 50, 2451-2458 (2001).

The subject animals were kept in macrolon cages at 22-24° C. and 50-60% humidity, with lighting regimen of 12 hours light/12 hours dark. The animals had free access to tap water and were fed a sterilized standard diet (Charles River VRF1, autoclavable; Germany) according to the provided instructions. The animals were cared for according to "Guiding Principles for the Care and Use of Animals" based upon the Helsink Declaration.

For treated and control NOD animals (180 days old), blood samples were taken from the eye corner, and initial blood glucose levels (day 1) were determined by the Fast Glucose C test. Over an eleven-day period, a solution of commercial PALP (30 mg/mL in physiological saline) was injected into four treated animals (1.5 mg/mouse) subcutaneously (s.c) or intraperitonialiy (i.p.) at four times. Injections were given on days 1, 3, 5 and 8. On day 11, blood samples were taken from the eye corner for both treated and control animal, and blood glucose levels were determined by the Fast Glucose C test.

As indicated by the data in Table 2, for the three untreated NOD mice, blood glucose concentrations increased by 7.2-8.4 mM during the 11-day period. In contrast, in the four animals treated with PALP subcutaneously, the increases in blood glucose levels were considerably lower (in the range of 0.6-3.1 mM). For animals treated with PALP intraperitonially, there was a similar reduction in the increase (in the range of 0.7-3.4 mM) in blood glucose levels (data not given in Table 2).

TABLE 2

Changes in blood glucose levels observed for untreated and PALP-treated NOD mice.

| | Untreated Mice | | | PALP-Treated Mice (subcutaneous) | | | |
|---|---|---|---|---|---|---|---|
| | Subject | | | | | | |
| | 1 | 2 | 3 | 1 | 2 | 3 | 4 |
| | Blood glucose level (mM) | | | Blood glucose level (mM) | | | |
| Day 1 | 12.7 | 8.2 | 12.9 | 7.9 | 12.9 | 8.1 | 13.3 |
| Day 11 | 20.8 | 15.4 | 21.3 | 8.5 | 16.0 | 8.7 | 16.2 |
| Increase | 8.1 | 7.2 | 8.4 | 0.6 | 3.1 | 0.6 | 2.9 |
| Survival (days) | 12 | 22 | 16 | <150 | 25 | <150 | 27 |

Also, it was observed that the untreated mice survived for not longer than 22 days; in contrast, PALP-treated mice survived for at least 25 days, and up to over 150 days in some cases.

In this set of experiments, no attempt was made to examine the potentially stronger effects of administering a greater quantity of PALP. The results clearly indicate that administration of PALP markedly reduces the rise in blood glucose levels in the non-obese Type 1 diabetic model.

Example 7

Determination of Blood Glucose Levels in Untreated and PALP-treated Obese Diabetic Mice In this set of experiments, the effect of PALP on blood glucose levels was determined in obese diabetic adult female mice. Data for the experiments is given in Table 3.

Obese diabetic inbred adult (six weeks old) female C57Bl/6J Bom-ob mice weighing 33–37 g were obtained from Charles River Laboratories, Germany. These animals are in the specified pathogen-free (SPF) hygienic category. A mutation in the leptin gene, responsible for obesity, was propagated in the C57Bl/6J (B1/6) inbred strain These homozygous obese (ob/ob) animals developed hyperglycemia, hyperinsulinemia and obesity by six weeks of age. Food intake is greatly increased by that time.

The subject animals were kept in macrolon cages at 22-24° C. and 50-60% humidity, with lighting regimen of 12 hours light/12 hours dark. The animals had free access to tap water and were fed with a sterilized standard diet (Charles River VRF1, autoclavable) according to the prescribed standard. The animals were cared for according to "Guiding Principles for the Care and Use of Animals" as stated in the Helsinki Declaration.

On day 43 (Day 1 in Table 3), the animals were divided into five groups (I-V) each consisting of four animals, and the treatments started as specified in Table 3. Animals with similarly high blood glucose levels were selected for each of groups I-V. In short, the treatments were: untreated (Group I); treated with commercial PALP for 28 days, 5 times/week, intraperitonially (Group II); treated with commercial PALP for 28 days, 3 times/week, intraperitonially (Group III); treated with commercial PALP for 28 days, 5 times/week, subcutaneously (Group IV); treated with commercial PALP for 28 days, 3 times/week, subcutaneously (Group V). Initially, each treatment consisted of 1.5 mg commercial PALP/mouse in physiological saline; then on day 15 (Group II and IV) or day 16 (Group II and V) the dosage of commercial PALP was increased to 3 mg/mouse. Blood samples were analyzed for glucose on the days indicated in the table. Blood glucose level (BGL) data are the mean ±S.E. of single simultaneous determinations from four animals of the group.

Data is tabulated in Table 3. For the untreated animals of Group I, blood glucose levels increased steadily over the 28 days period. However, for both intraperitoneal (Groups II and III) and subcutaneous administration (Groups IV and V) of PALP, a steady decrease in blood glucose was observed for the subject animals. The data further indicate that the 1.5 mg PALP/mouse dosage was effective in decreasing the blood glucose level, while the 3 mg/mouse dosage was slightly more effective.

It should be noted that intraperitoneal and subcutaneous treatments were similarly effective, with intraperitoneal administration providing somewhat better results. It is also noteworthy that treatment 5 times/week was only slightly more effective than treatment 3 times/week for either intraperitoneal or subcutaneous administration. The data suggests that, in humans, daily administration may not be required in order to effectively control hyperglycemia.

mediated regulation, ob/ob animals gain substantial weight, leading gradually and inevitably to decreased insulin sensitivity in the peripheral tissues such as muscle, adipose tissue, and liver. As a consequence, in ob/ob animals the blood glucose level is high due to impaired uptake and metabolism of glucose by the peripheral tissues, and to increased production of glucose by the liver, which is normally inhibited by insulin. The obesity syndrome in ob/ob mice can be corrected by administration of leptin [B. M. Spiegelman and J. S. Flier, "Obesity and the regulation of energy balance." *Cell* 104, 531-543 (2001)].

Importantly, high glucose levels that are induced by physiological events other than obesity do not lead to obesity. Also, lowering of glucose level does not necessarily lead to weight loss; i.e., high glucose level is not a risk factor for obesity. For example, some of the most important agents that are used to treat diabetes by lowering blood glucose level, including insulin, sulphonylureas and thiazolidinediones, can cause

TABLE 3

Changes in blood glucose levels observed for untreated and PALP-treated obese diabetic mice. (BGL = Blood Glucose Level (mM))

| Day | Group I BGL ± S.E. | Group II intraperitoneal BGL ± S.E. | Group II intraperitoneal PALP | Group III intraperitoneal BGL ± S.E. | Group III intraperitoneal PALP | Group IV subcutaneous BGL ± S.E. | Group IV subcutaneous PALP | Group V subcutaneous BGL ± S.E. | Group V subcutaneous PALP |
|---|---|---|---|---|---|---|---|---|---|
| 1 | 5.6 ± 0.7 | 7.2 ± 0.2 | 1.5 mg | 7.6 ± 0.9 | | 7.1 ± 0.5 | 1.5 mg | 7.3 ± 0.5 | |
| 2 | — | 7.3 ± 0.2 | 1.5 mg | 7.6 ± 0.8 | 1.5 mg | 7.1 ± 0.4 | 1.5 mg | 7.3 ± 0.6 | 1.5 mg |
| 3 | 5.8 ± 0.9 | 6.6 ± 0.2 | 1.5 mg | 7.1 ± 0.6 | | 6.7 ± 0.2 | 1.5 mg | 7.3 ± 0.6 | |
| 4 | — | 6.4 ± 0.3 | 1.5 mg | 6.8 ± 0.2 | 1.5 mg | 6.8 ± 0.1 | 1.5 mg | 6.8 ± 0.4 | 1.5 mg |
| 5 | 6.2 ± 0.6 | 5.4 ± 0.3 | 1.5 mg | 6.4 ± 0.5 | | 6.5 ± 0.1 | 1.5 mg | 6.4 ± 0.3 | |
| 7 | — | 5.1 ± 0.2 | 1.5 mg | 6.1 ± 0.7 | 1.5 mg | 6.3 ± 0.2 | 1.5 mg | 6.2 ± 0.5 | 1.5 mg |
| 8 | 7.6 ± 1.2 | 5.0 ± 0.5 | 1.5 mg | 5.5 ± 0.7 | | 6.1 ± 0.1 | 1.5 mg | 5.8 ± 0.3 | |
| 9 | — | 5.2 ± 0.2 | 1.5 mg | 5.7 ± 0.6 | 1.5 mg | 6.1 ± 0.2 | 1.5 mg | 5.7 ± 0.5 | 1.5 mg |
| 10 | 7.9 ± 0.2 | 4.5 ± 0.3 | 1.5 mg | 5.5 ± 0.6 | | 6.1 ± 0.3 | 1.5 mg | 5.5 ± 0.6 | |
| 11 | — | 4.4 ± 0.3 | 1.5 mg | 5.2 ± 0.4 | 1.5 mg | 5.9 ± 0.3 | 1.5 mg | 5.3 ± 0.4 | 1.5 mg |
| 14 | 8.6 ± 1.3 | 4.6 ± 0.2 | 1.5 mg | 5.1 ± 0.5 | 1.5 mg | 5.7 ± 0.3 | 1.5 mg | 5.3 ± 0.4 | 1.5 mg |
| 15 | — | 4.4 ± 0.1 | 3 mg | 4.8 ± 0.4 | | 5.2 ± 0.3 | 3 mg | 5.0 ± 0.4 | |
| 16 | 8.8 ± 0.4 | 3.5 ± 0.3 | 3 mg | 4.4 ± 0.4 | 3 mg | 4.1 ± 0.2 | 3 mg | 4.2 ± 0.2 | 3 mg |
| 17 | — | 2.9 ± 0.2 | 3 mg | 3.4 ± 0.2 | | 3.7 ± 0.2 | 3 mg | 3.6 ± 0.2 | |
| 18 | 8.0 ± 0.2 | 2.7 ± 0.2 | 3 mg | 3.1 ± 0.2 | 3 mg | 3.5 ± 0.1 | 3 mg | 3.4 ± 0.3 | 3 mg |
| 21 | — | 2.5 ± 0.2 | 3 mg | 2.9 ± 0.3 | 3 mg | 3.4 ± 0.3 | 3 mg | 3.3 ± 0.2 | 3 mg |
| 22 | 8.6 ± 0.5 | 2.3 ± 0.2 | 3 mg | 2.7 ± 0.2 | | 3.6 ± 0.2 | 3 mg | 3.0 ± 0.4 | |
| 23 | — | 2.4 ± 0.3 | 3 mg | 2.5 ± 0.1 | 3 mg | 3.1 ± 0.1 | 3 mg | 2.6 ± 0.3 | 3 mg |
| 24 | 8.8 ± 0.5 | 2.3 ± 0.1 | 3 mg | 2.2 ± 0.2 | | 2.9 ± 0.2 | 3 mg | 2.6 ± 0.3 | |
| 25 | — | 2.0 ± 0.2 | 3 mg | 2.1 ± 0.3 | 3 mg | 2.8 ± 0.2 | 3 mg | 2.5 ± 0.3 | 3 mg |
| 28 | 8.5 ± 0.4 | 1.5 ± 0.1 | | 1.6 ± 0.1 | | 2.3 ± 0.3 | | 2.3 ± 0.2 | |

Example 8

Effect of PALP Treatment on Body Weight for Obese Diabetic Mice

Obesity is characterized by an increase in adipose tissue and body weight to a level that produces adverse health effects, including increased risk for development of diabetes. White adipose tissue secretes several factors that regulate energy balance and whole-body homeostasis; one of the most important such factors is the hormone leptin [F. M. Gregoire, "Adipocyte differentiation: From fibroblast to endocrine cell" *Exp. Biol. Med.* 226, 997-2001 (2001)].

The gene responsible for leptin production is called the ob gene. In ob/ob animals, the leptin secreted from the adipose tissue is truncated and thereby inactivated [B. M. Spiegelman and J. S. Flier, "Obesity and the regulation of energy balance." *Cell* 104, 531-543 (2001)]. Due to the absence of leptin-significant weight gain [see Table 1 in D. E. Moller, "New drug targets for type 2 diabetes and the metabolic syndrome." *Nature* 414, 821-827 (2001)], while biguanides (e.g., metformin) can cause moderate weight gain [U.K. Prospective Diabetes Study Group, "U.K Prospective Diabetes Study 16. Overview of 6 years' therapy of Type 2 diabetes: A progressive disease." *Diabetes* 44, 1249-1258 (1995)]. None of the presently used glucose-lowering agents are known to cause weight loss.

In view of the differential regulation of adipose tissue weight and blood glucose level, it was of interest to determine whether administration of PALP also modifies body weight that primarily results from increased weight of adipose tissue in ob/ob mice. Accordingly, in the experiment described in Example 7, the body weight of untreated and PALP-treated obese diabetic mice was also regularly measure. The schedule of treatments and the results are given in Table 4.

TABLE 4

Effect of administration of PALP on body weight of obese diabetic mice.

| Day | Group I Body weight (g) ± S.E. | Group II intraperitoneal Body weight (g) ± S.E. | PALP | Group III intraperitoneal Body weight (g) ± S.E. | PALP | Group IV subcutaneous Body weight (g) ± S.E. | PALP | Group V subcutaneous Body weight (g) ± S.E. | PALP |
|---|---|---|---|---|---|---|---|---|---|
| 1 | 35.5 ± 0.9 | 37.2 ± 1.3 | 1.5 mg | 33.3 ± 1.7 | | 33.5 ± 0.6 | 1.5 mg | 33.0 ± 0.7 | |
| 2 | 34.4 ± 1.0 | 36.7 ± 0.6 | 1.5 mg | 31.7 ± 1.6 | 1.5 mg | 32.1 ± 1.0 | 1.5 mg | 31.6 ± 1.1 | 1.5 mg |
| 3 | 35.5 ± 0.8 | 36.3 ± 0.5 | 1.5 mg | 32.2 ± 1.4 | | 31.7 ± 1.0 | 1.5 mg | 32.7 ± 0.8 | |
| 4 | 35.6 ± 0.9 | 35.8 ± 0.7 | 1.5 mg | 31.7 ± 1.9 | 1.5 mg | 31.5 ± 0.9 | 1.5 mg | 31.6 ± 0.5 | 1.5 mg |
| 5 | 36.0 ± 1.1 | 35.3 ± 0.7 | 1.5 mg | 31.8 ± 1.5 | | 32.1 ± 1.2 | 1.5 mg | 31.7 ± 0.5 | |
| 7 | 37.3 ± 0.9 | — | 1.5 mg | 32.3 ± 1.3 | 1.5 mg | 32.9 ± 0.9 | 1.5 mg | 33.2 ± 0.3 | 1.5 mg |
| 8 | 38.5 ± 1.3 | 35.9 ± 0.6 | 1.5 mg | 32.2 ± 2.1 | | 33.4 ± 0.6 | 1.5 mg | 32.4 ± 1.1 | |
| 9 | 38.0 ± 1.8 | 35.4 ± 0.8 | 1.5 mg | 32.2 ± 1.6 | 1.5 mg | 33.7 ± 0.9 | 1.5 mg | 32.8 ± 0.6 | 1.5 mg |
| 10 | 37.9 ± 1.0 | 35.3 ± 0.5 | 1.5 mg | 32.3 ± 1.6 | | 33.7 ± 1.6 | 1.5 mg | 32.2 ± 0.5 | |
| 11 | 37.9 ± 1.3 | 35.0 ± 0.4 | 1.5 mg | 32.3 ± 1.9 | 1.5 mg | 33.8 ± 1.9 | 1.5 mg | 32.9 ± 0.4 | 1.5 mg |
| 14 | 39.7 ± 1.2 | 33.9 ± 1.0 | 1.5 mg | 33.0 ± 1.2 | 1.5 mg | 34.8 ± 2.3 | 1.5 mg | 34.2 ± 1.0 | 1.5 mg |
| 15 | 39.7 ± 1.0 | 34.0 ± 1.9 | 3 mg | 33.0 ± 1.9 | | 36.0 ± 1.0 | 3 mg | 33.7 ± 0.5 | |
| 16 | 39.9 ± 1.4 | 33.8 ± 0.8 | 3 mg | 32.9 ± 2.1 | 3 mg | 34.7 ± 2.1 | 3 mg | 33.9 ± 0.5 | 3 mg |
| 17 | 39.8 ± 1.5 | 33.5 ± 1.1 | 3 mg | 32.6 ± 2.2 | | 34.8 ± 2.2 | 3 mg | 33.8 ± 0.4 | |
| 18 | 40.1 ± 1.3 | 33.3 ± 1.0 | 3 mg | 32.8 ± 2.3 | 3 mg | 35.2 ± 1.6 | 3 mg | 34.1 ± 0.4 | 3 mg |
| 21 | 41.4 ± 1.7 | 33.6 ± 1.2 | 3 mg | 33.7 ± 2.4 | 3 mg | 36.2 ± 1.7 | 3 mg | 36.2 ± 0.7 | 3 mg |
| 22 | 41.7 ± 1.6 | 33.1 ± 1.8 | 3 mg | 33.5 ± 1.8 | | 35.9 ± 1.7 | 3 mg | 36.0 ± 1.0 | |
| 23 | 41.6 ± 2.8 | — | 3 mg | 33.4 ± 2.3 | 3 mg | 35.6 ± 1.7 | 3 mg | — | 3 mg |
| 24 | 41.8 ± 2.0 | — | 3 mg | 33.2 ± 1.5 | | 35.8 ± 1.6 | 3 mg | — | |
| 25 | 41.6 ± 1.4 | 32.2 ± 1.3 | 3 mg | 32.6 ± 1.4 | 3 mg | 36.1 ± 2.1 | 3 mg | 37.1 ± 0.8 | 3 mg |
| 28 | 43.7 ± 2.7 | 32.8 ± 0.8 | | 32.9 ± 1.4 | | 37.4 ± 1.6 | | 37.4 ± 1.0 | |
| % Gain | 23.1% | −11.8% | | −1.2% | | 11.6% | | 13.3% | |

Untreated animals of Group I steadily gained weight over the 28-day observation period, with body weight increasing approximately 23% overall. In contrast, animals treated with PALP administered intraperitoneally five times per week (Group II) actually decreased in weight by approximately 12% overall, while animals treated with PALP administered intraperitoneally three times per week essentially maintained their weight (Group III). Animals treated with PALP five times per week (Group IV) administered subcutaneously, or three times per week (Group V) administered subcutaneously gained about half as much weight as the control group.

Because intraperitoneal and subcutaneous treatments had similar effects on the blood glucose level (Table 3), the clearly established ability to achieve weight control by intraperitoneally administering PALP may involve some mechanism in addition to the control of glucose level. In fact, considering that for the ob/ob model obesity leads to insulin insensitivity and higher blood glucose levels, but not vice-versa, it is likely that in this model a primary mode of action of PALP was weight control, and that the reduction in blood glucose level was a secondary effect. The mechanism by which PALP achieves weight control is not known. However, since the absence of functional leptin hormone is responsible for obesity in ob/ob animals, it is reasonable to assume that PALP acts as a substitute for the most important weight control-related functions of leptin.

Examples 9-12

Effects of PALP on Glucose Uptake and Metabolism in Differentiated 3T3-L1 Adipocytes and Rat L6 Cells at Different Levels of Glucose and Serum in the Medium The above-described experiments suggested that PALP decreased the blood glucose level in treated mice by stimulating glucose uptake and metabolism in peripheral tissues, which explains the relatively long time required for body distribution and action. This hypothesis was examined for differentiated adipocytes and muscle cells.

Mouse 3T3-L1 pre-adipocyte cells and rat L6 skeletal muscle cells were obtained from the American Type Culture Collection (Rockville, Md.). 3T3-L1 cells were grown in high-glucose Dulbecco's modified Eagle medium (DMEM) supplemented with 10% (v/v) fetal bovine serum (FBS) and 1% antibiotic/antimycotic (GIBCO, Grand Island, N.Y.) composed of 10,000 units/mL penicillin G, 10 mg/mL streptomycin, and 25 µg/mL amphotericin B.

To induce cell differentiation of the two cell lines, conventional methods were used, as follows. 3T3-L1 cells were maintained in a state of confluency for 2 days, followed by treatments for 3 days with 400 nM insulin (Boehringer Mannheim, Indianapolis, In.), 250 nM dexamethasone (Sigma-Aldrich, Inc., St. Louis, Mo.) and 0.5 mM isobutyimethylxanthine (Sigma-Aldrich, Inc.). The medium was replaced with fresh 10% serum containing medium, and the medium was changed twice a week. The differentiated cells were used 14 days after removing the differentiation-inducing agents.

The L6 cells in monolayer culture were induced to differentiate in minimal essential medium (MEM) containing 2% (v/v) FBS and 1% (v/v) antibiotic/antimycotic solution. The cells were fed fresh medium every 48 hours. Myoblast differentiation, which occurred by about the seventh day, was monitored by phase contrast microscopy.

To examine cellular glucose uptake and metabolism, differentiated (attached) cells in 12-well plates were incubated with D-[$^{14}$C]glucose at 37° C. in a $CO_2$ incubator (95% air. 5% $CO_2$) in 2% serum or 10% serum-containing (as specified in the specific examples) glucose-free or 5 mM D-glucose-containing medium for 2-6 hours. In the various experiments, the quantity of other reagents (such as PALP or insulin) in the incubation medium was varied, as specified.

At the termination of incubation, the medium was removed; an aliquot of the medium was taken to determine the loss of D-[$^{14}$C]glucose from the medium, which corresponds to glucose uptake by cells. Cells were washed twice with 3—3 mL medium to remove traces of medium containing unincorporated radioactivity. Then ice-cold 99.8% methanol/02% water (v/v) mixture (1 m) was added to the monolayers, and cells were extracted for 2 hours at −20° C. This treatment resulted in the precipitation of glycogen and the solubilization of cellular free glucose and lipids.

Precipitated [$^{14}$C]glycogen was suspended in 0.75 mL of 1 M NaOH and transferred to scintillation vials; this procedure was repeated with another 0.75 mL aliquot of NaOH 10 mM HCl (~150 µL) was added to the vials to neutralize the suspension, followed by the addition of 8.5 mL ECOLUME (ICN Pharmaceuticals, Inc., Costa Mesa, Calif.). While the 1 M NaOH suspension contained some particulate material (mostly protein which was not labeled with radiolabeled glucose), after transfer to ECOLUME no precipitate remained. This procedure resulted in quantitative removal of precipitated glycogen; no additional radioactivity could be removed from the well by 30% KOH (which was neutralized with HCl prior to determination of radioactivity).

The methanol mixture containing cellular free glucose and lipids was treated as follows. The methanol phase (1 ml) and a following 1 mL methanol wash were added to 2 mL chloroform, followed by the addition of 3 mL water. Separation of this organic-aqueous mixture was facilitated by brief centrifugation. Of the resulting two phases, the lower one contained the total radiolabeled lipids, while the upper one contained radiolabeled glucose. Aliquots of the upper and lower phases were transferred to scintillation vials to determine the amounts of radiolabeled glucose and total lipids, respectively, by liquid scintillation counting.

In some experiments, a published procedure [Huang, D., Cheung, A. T., Parsons, J. T. and Bryer-Ash, M., "Focal adhesion kinase OAK) regulates insulin-stimulated glycogen synthesis in hepatocytes." *J. Biol. Chem.* 277, 18151-18160 (2002)] parallel to the above method was used to determine glucose incorporation into glycogen. After incubations with D-[$^{14}$C]glucose, cells were solubilized with 20% KOH for 2 hours. Lysates were extracted with 8% tricarboxylic acid, neutralized with 2.0 M HCl, then boiled for 5 minutes. Total glycogen was precipitated by the addition of 80% ethanol (final concentration) for 2 hours at −20° C. followed by centrifugation at 1100×g for 10 minutes. Precipitation and centrifugation was repeated. The precipitate was then re-dissolved in distilled water, and the solids were precipitated again as before. This method yielded essentially the same results as the methanol precipitation method described above. Thus, in all subsequent experiments we used the methanol precipitation method because this permitted simultaneous analysis of cellular glucose, glycogen and lipids for an individual sample.

Example 9

Stimulatory Effect of PALP on Glucose Uptake in Differentiated L1 cells

Three groups of differentiated L1 cells (used 14 days after the differentiation treatment described above) in 12-well plates were treated as follows: a first control group was untreated; a second group was treated with 0.75 mL of a preparation comprising 0.5 U/mL commercial PALP in serum free and glucose-free DMEM for 30 minutes, and a third group was treated with 0.75 mL of a preparation comprising 1.0 U/mL commercial PALP in se free and glucose-free DMEM for 30 minutes. The following experiment was performed in triplicate for each group.

Each group was then incubated as described above for 5 hours following addition of D-[$^{14}$C]glucose, under four different conditions as follows: (1) the incubation medium contained no serum or unlabeled D-glucose; (2) the incubation medium contained 2% fetal bovine serum (FBS) but no unlabeled D-glucose; (3) the incubation medium contained 5 mM unlabeled D-glucose but no serum; and (4) the incubation medium contained 5 mM unlabeled D-glucose +2% FBS.

Figure 5:
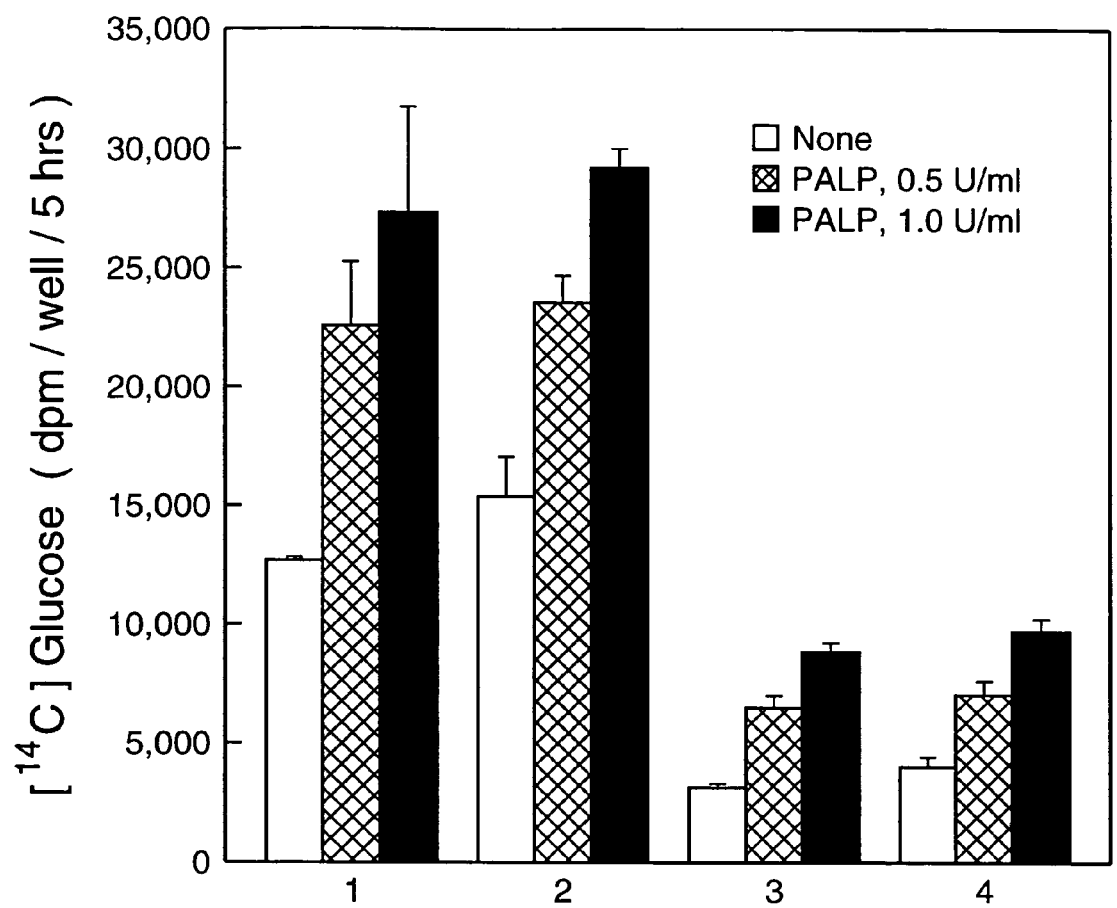
FIG. 5 indicates that in differentiated L1 adipocyte cells, commercial PALP stimulates cellular uptake of D-[$^{14}$C]glucose at various levels of glucose and serum in the incubation medium.

For each condition for each group, the amount of radiolabeled glucose was determined by liquid scintillation counting. Results are charted in FIG. 5. The data are the mean±S.D. of three determinations for each group under each condition. Under each of the four conditions, treatment with PALP at both 0.5 U/mL (◉) and 1.0 U/mL (■) concentrations enhanced the cellular content of D-[$^{14}$C]glucose approximately two fold or more, relative to the untreated control group (□). In the presence of 5 nM unlabeled D-glucose (conditions 3 and 4), L1 cells obviously incorporated less D[$^{14}$C]glucose (because of greatly decreased specific activity; at the same time PALE bad somewhat greater stimulatory effects on D-[$^{14}$C]glucose uptake compared to its effect in glucose-free medium. The experiment was repeated for each group at least once, with similar results.

Example 10

Figure 6:
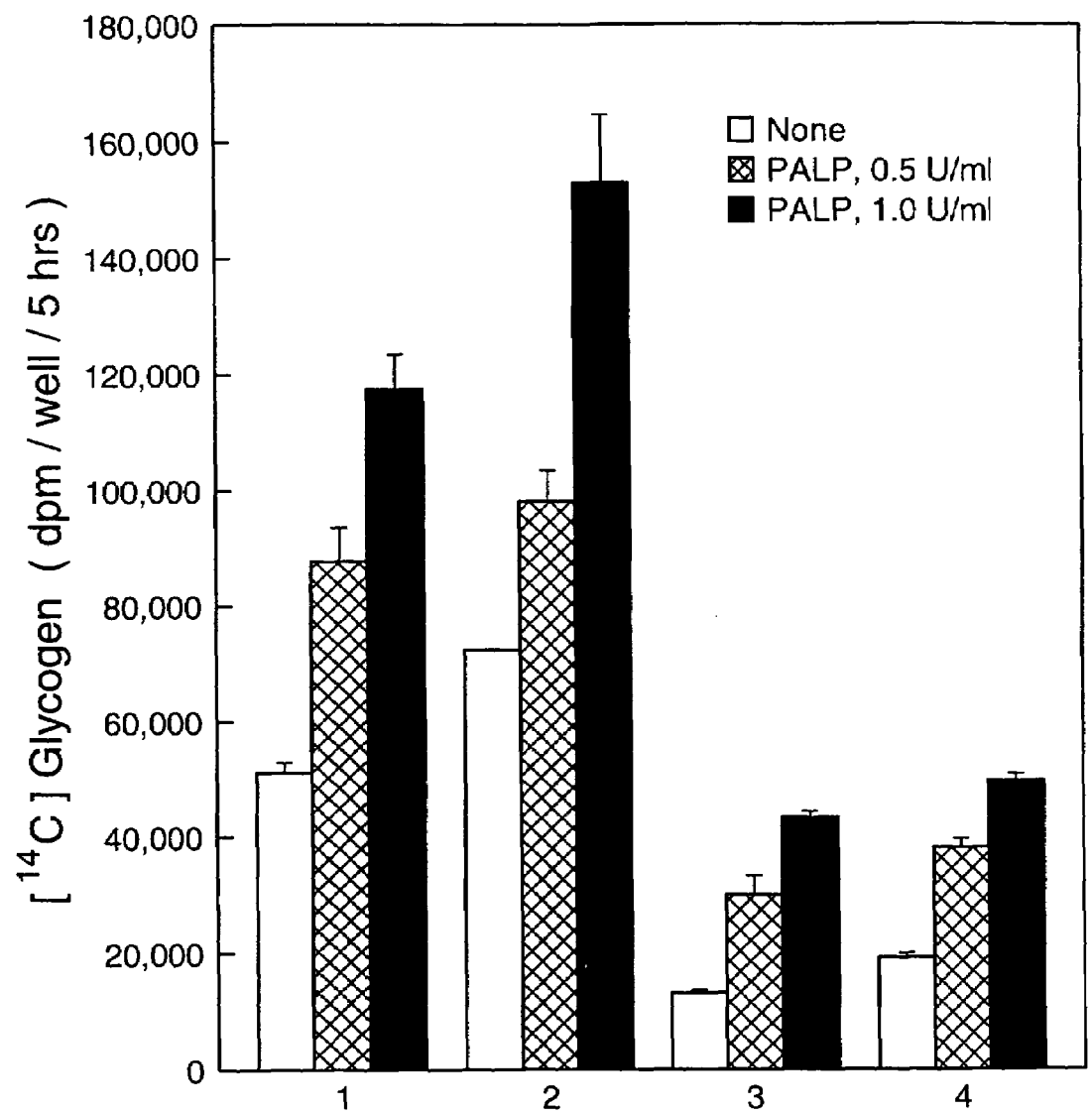
FIG. 6 demonstrates that in differentiated L1 adipocyte cells, commercial PALP stimulates the cellular synthesis of glycogen from D-[$^4$C]glucose at various compositions of the incubation medium.

Stimulatory Effect of PALP on Cellular Synthesis of [$^{14}$C]glycogen from D-[$^{14}$C]glucose The same conditions as described in Example 9 were used, except the amount of radiolabeled glycogen was determined by liquid scintillation counting. Results are charted in FIG. 6. Treatments included PALP at 0.5 U/mL (◉) and 1.0 U/mL (■), and the untreated control group (□). Again, while in the presence of 5 mM unlabeled D-glucose L1 cells obviously incorporated less D-[$^{14}$C]glucose into glycogen, in the presence of 5 mM D-glucose PALP had slightly greater (~2 to ~3-fold) stimulatory effects on the synthesis of [$^{14}$C]glycogen.

Example 11

Figure 7:
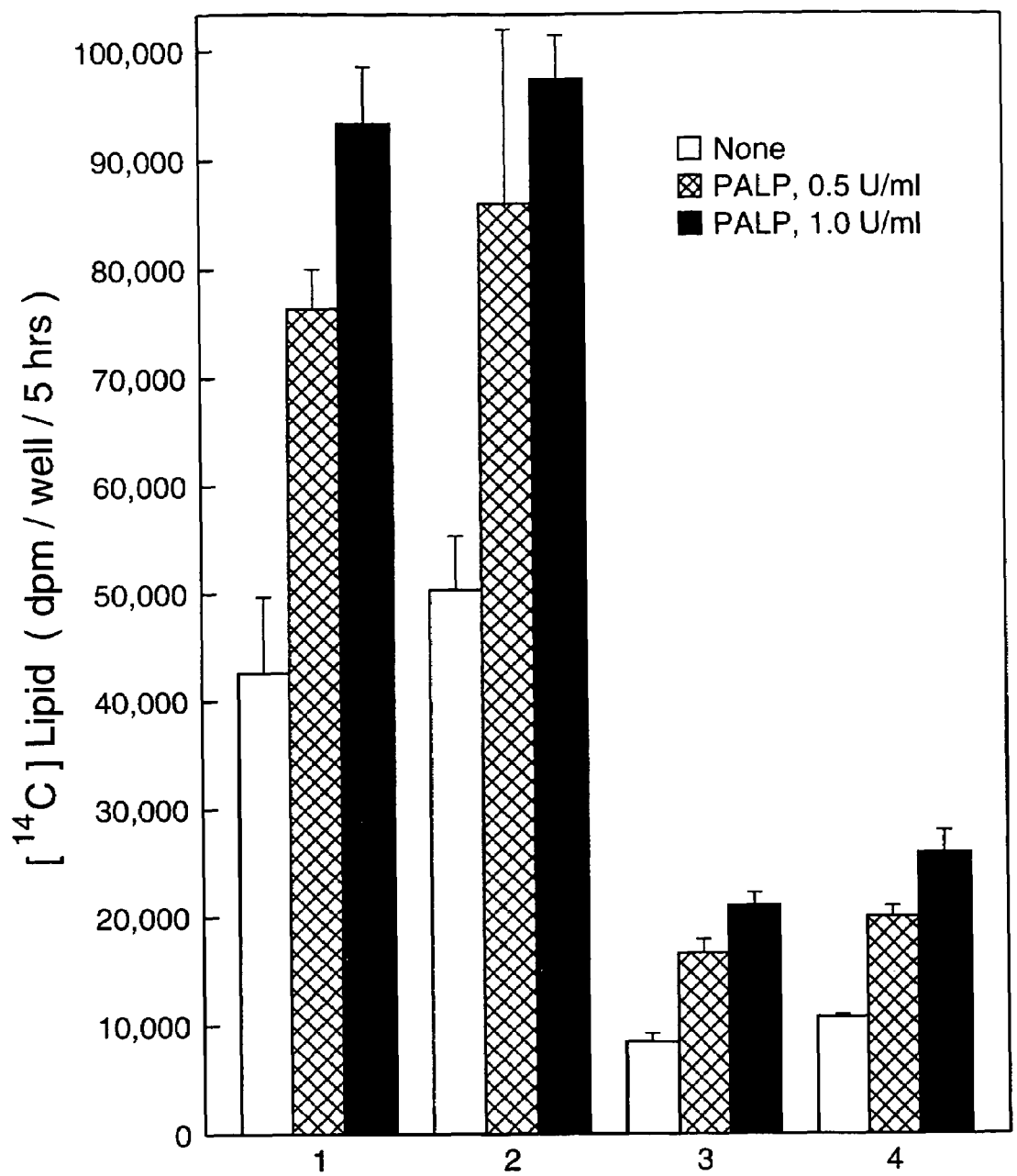
FIG. 7 demonstrates that in differentiated L1 adipocyte cells, commercial PALP stimulates the cellular synthesis of lipids from D-[$^{14}$C]glucose at various compositions of the incubation medium.

Stimulatory Effect of PALP on the Incorporation of D-[$^{14}$C]glucose into the Total Lipid Fraction The same conditions as described in Example 9 were used, except the amount of total radiolabeled lipids was determined by liquid scintillation counting. Results are charted in FIG. 7. Treatments included PALP at 0.5 U/mL (◉) and 1.0 U/mL (■), and the untreated control group (□). Although in the presence of 5 mM unlabeled D-glucose cells incorporated less D-[$^{14}$C]glucose into lipids, as expected, PALP had slightly greater (~2 to ~2.5-fold) stimulatory effects on [$^{14}$C] lipid synthesis compared to its effects in the absence of D-glucose.

Overall the experiments described in Examples 9-11 indicate that, in differentiated L1 cells, PALP clearly stimulates cellular uptake and metabolism of D-glucose, that PALP is more effective at 1 U/mL than at 0.5 U/mL concentration, and that the effects of PALP do not strongly depend on the concentration of glucose in the medium. These experiment strongly suggest that a primary target of PALP in mice, and by extension in humans, is fat tissue.

Example 12

Stimulatory Effect of PALP on Glucose Metabolism in Differentiated L6 Cells

Another potential target of PALP may be the skeletal muscle. The effects of PALP on glucose uptake/metabolism were determined in differentiated L6 cells, a widely used model for skeletal muscle.

Figure 8:
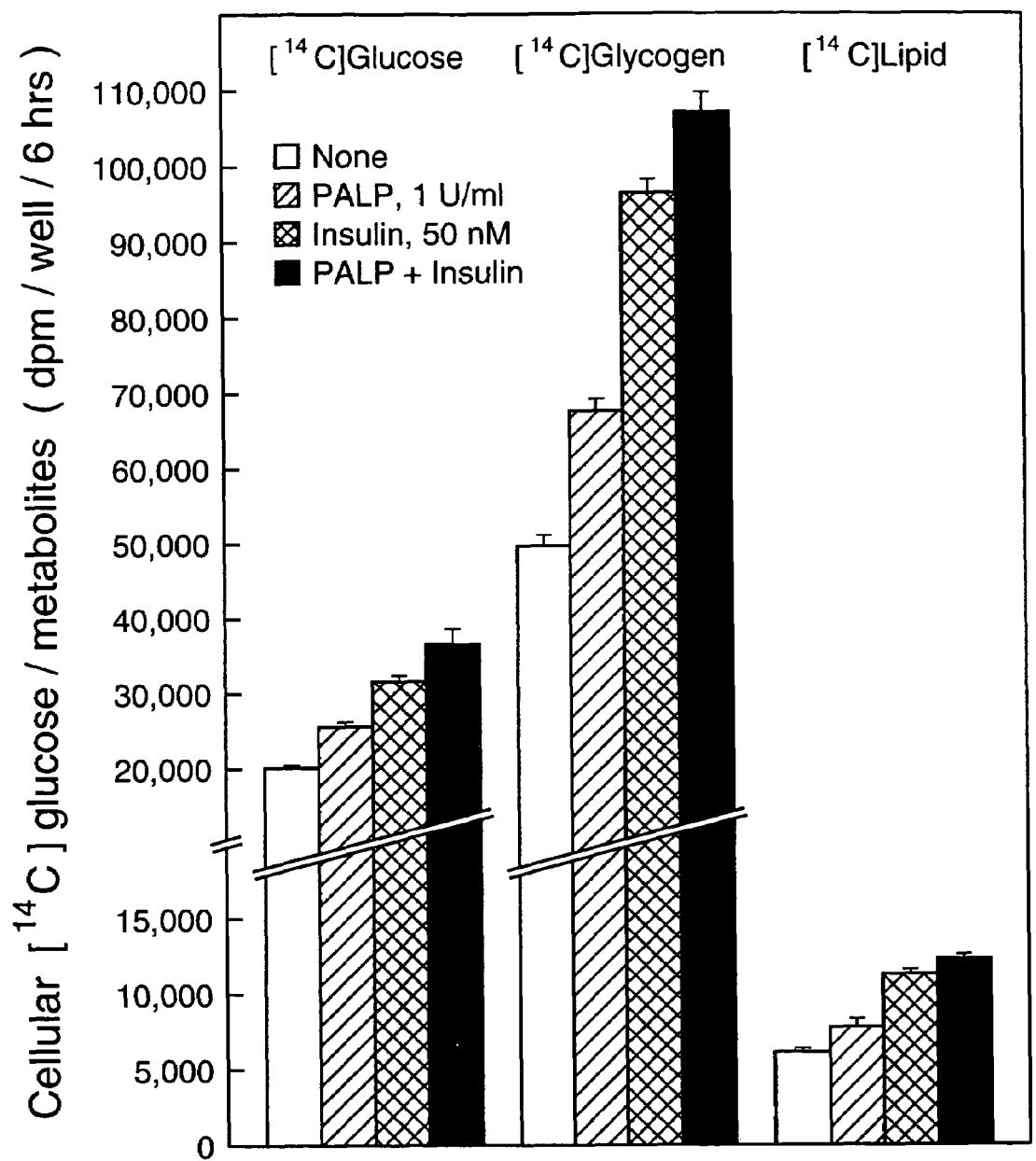
FIG. 8 demonstrates that in differentiated L6 muscle cells, both 1 U/mL commercial PALP and 50 nM insulin enhance the uptake and metabolism of D-[$^{14}$C]glucose after treatments for 6 hours; PALP and insulin in combination had approximately additive effects.

Differentiated L6 cells in 12-well plates were incubated in 2% FBS-containing MEM for 6 hours with 1 µCi/mL of D-[$^{14}$C]glucose in the absence (□) or presence of 1 U/mL commercial PALP (▨), 50 nM insulin ("Ins") (▩), or 1 U/mL commercial PALP+50 nM Ins (■). The data, shown in FIG. 8, are the mean ±S.D. of three determinations in one experiment (the experiment was repeated once with similar results).

PALP clearly stimulated, although only slightly, both the cellular uptake of D-[$^{14}$C]glucose and its metabolism to [$^{14}$C]glycogen and [$^{14}$C]total lipid for the differentiated L6 cells. Insulin was at least 50% more effective than PALP in stimulating all three mechanisms, and in each case the effects of PALP plus insulin were roughly additive or less than additive.

Examples 13 and 14

Digestion with Protease Does Not Reduce the Effects of PALP on Glucose Metabolism

Example 13

Digestion of PALP by Bromelain

Bromelain (BRL) is a protease which was previously shown to effectively digest PALP leading to the formation of fragments of lower molecular mass [Kottel, R. H. and Hanford, W. C., "Differential release of membrane-bound alkaline phosphatase isoenzymes from tumor cells by bromelain." *Biochem Biophys. Methods* 2, 325-330 (1980)]. Based on this observation, bromelain was used to digest commercial PALP to determine if digestion by a protease can generate a smaller PALP fragment which is able to stimulate glucose metabolism.

Figure 9:
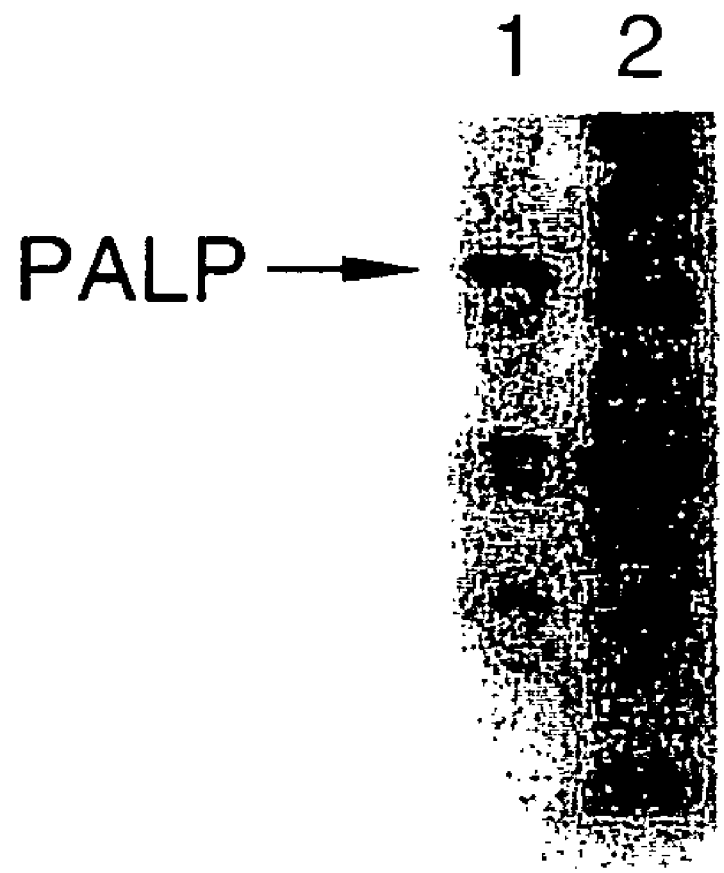
FIG. 9 shows a picture of a gel separation demonstrating that digestion of human PALP with bromelain results in the formation of a major fragment and several smaller fragments, concomitant with the disappearance of native PALP enzyme.

A preparation comprising 20 U/mL commercial PALP and 0.01 mg/mL of BRL (Sigma-Aldrich) in 1 mL of 25 mM Tris-HCl (pH7.4) buffer was incubated at 37° C. for 2 hours. FIG. 9 shows a gel picture (obtained by SDS-PAGE using 7.5% polyacrylamide) with undigested commercial PALP in lane 1 and BRL-digested PALP in lane 2. It is clear that, after digestion with 0.01 mg/mL of BRL, no detectable amount of the original PALP molecule remains.

Example 14

Effect of Bromelain Digestion Product of PALP on Glucose Metabolism

Differentiated L1 cells were preincubated in serum-free and glucose-free DMEM for two hours under the following conditions: (a) untreated; (b) in the presence of 1 U/mL commercial PALP; (c) in the presence of 0.01 mg/mL of BRL; and (d) in the presence of 1 U/mL commercial PALP+0.01 mg/mL BRL. Each group was then incubated for 5 hours in the presence of D-[$^{14}$C]glucose. Total radiolabeled lipids, radiolabeled glucose, and radiolabeled glycogen were determined by liquid scintillation counting, as described above.

Figure 10:
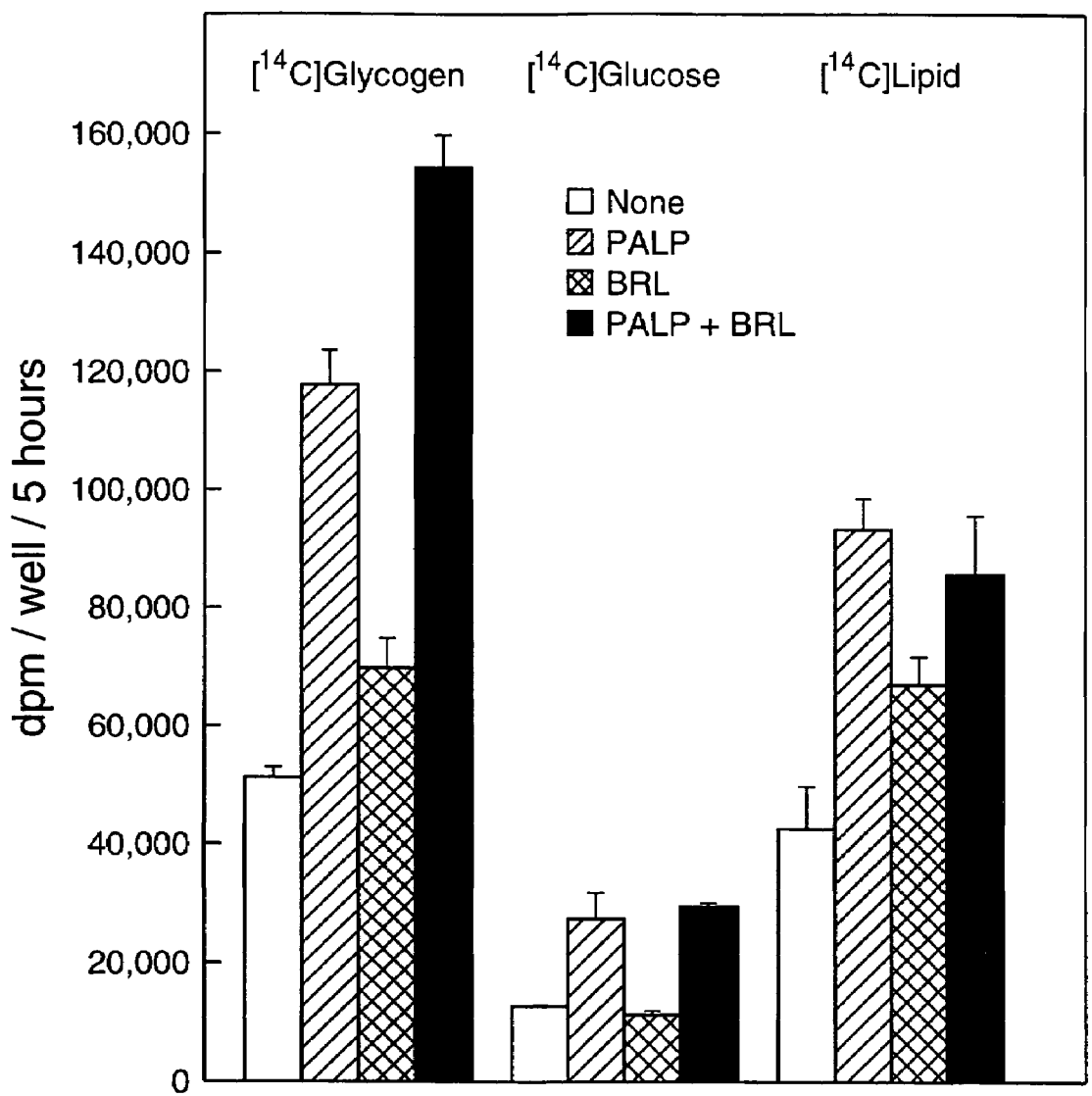
FIG. 10 demonstrates that in differentiated L1 adipocyte cells, a product of the digestion of human PALP by bromelain enhances the synthesis of glycogen, but not lipids, from D-[$^{14}$C]glucose, relative to native PALP. Bromelain did not affect the total cellular level of D-[$^{14}$C]glucose, but slightly enhanced glycogen and lipid synthesis.

Data is shown in FIG. 10. Treatment by BRL alone (▩) slightly enhanced both [$^{14}$C]glycogen and [$^{14}$C]lipid synthesis but had no clear effect on the cellular content of D-[$^{14}$C]glucose, relative to untreated cells (□). Treatment with the bromelain digestion product of PALP (■) enhanced glycogen synthesis, lipid synthesis, and glucose uptake relative to untreated cells (□). Treatment with the bromelain digestion product of PALP(■) slightly enhanced glycogen synthesis but not lipid synthesis, and had no clear effect on the cellular content of D-[$^{14}$C]glucose, relative to treatment by PALP (▨).

This experiment indicated that at least one PALP fragment (i.e. a sequence of PALP which is smaller than the full size PALP) at least partially retained the ability of native PALP to enhance glucose metabolism. Furthermore, the experiment also justifies the assumption that a fragment of PALP may be even more active in stimulating glycogen synthesis than native PALP. Potentially any sequence derived from PALP could be active in promoting glucose metabolism.

Examples 15-17

Comparison of the Effects of PALP and Insulin on Glucose Metabolism in Differentiated L1 Cells During the course of the experiments, it was observed that L1 cells respond better to PALP if the cells are used 8 to 11 days after terminating treatment with differentiation-inducing agents, as opposed to 14 days which was practiced in the previous experiments. Therefore, in the subsequent experiments we used L1 cells within 9 to 11 days after terminating treatment with differentiation-inducing agents.

Example 15

Effect of PALP and Ins on Glucose Content of Incubation Medium in Differentiated L1 cells In this experiment, differentiated L1 cells in 12-well plates were incubated (in 0.75 mL volume/well in 2% BFS-containing glucose-free DMEM for 6 hours with 1 µCi/mL of D-[$^{14}$C]glucose in the absence or presence of 1 U/mL commercial PALP or 50 nM Ins. At the conclusion of the experiment, 0.5 mL aliquots of the incubation medium were added to 9.5 mL ECOLUME, and the radioactivity was determined by scintillation counting. The data indicating loss of D-[$^{14}$C]glucose from the medium are the means±S.E.M. of three experiments each performed in triplicate.

Figure 11:
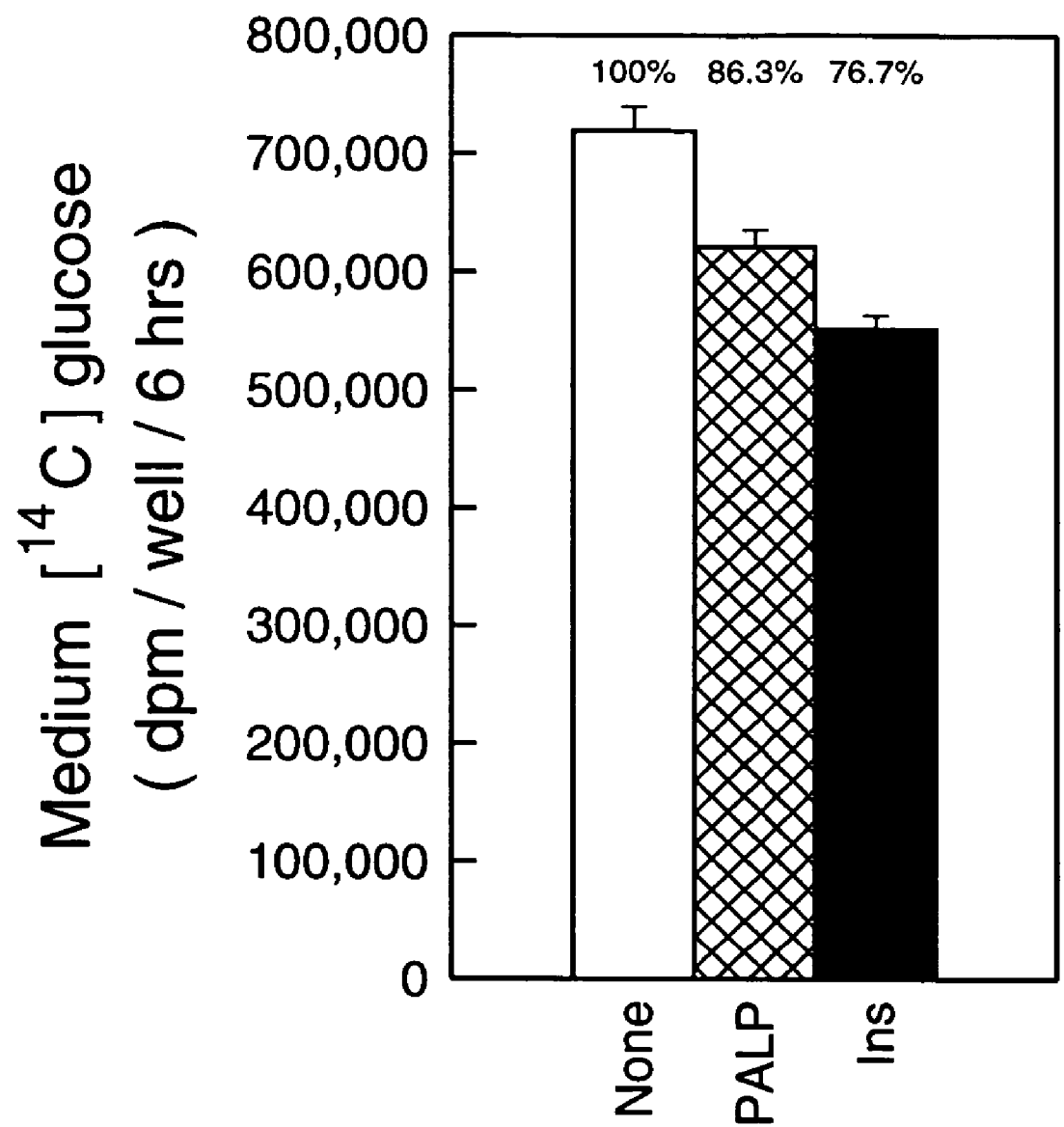
FIG. 11 demonstrates that in differentiated L1 adipocyce cells, treatment with either commercial PALP or insulin for 6 hours decreased the amount D[$^{14}$C]glucose in the incubation medium, indicating that both agents enhance cellular uptake of the radiolabeled glucose.

Data is graphed in FIG. 11. The experiment showed that treatment with PALP (▨) and 50 nM Ins (■) stimulated the loss of D-[$^{14}$C]glucose from the medium (i.e. uptake by the cells) by ~86% and 77%, respectively, relative to the untreated control (□). Thus, Ins, at the physiologically supramaximal 50 nM concentration, was more effective than PALP in increasing the uptake of D-[$^{14}$C]glucose by differentiated L1 cells.

Example 16

Figure 12:
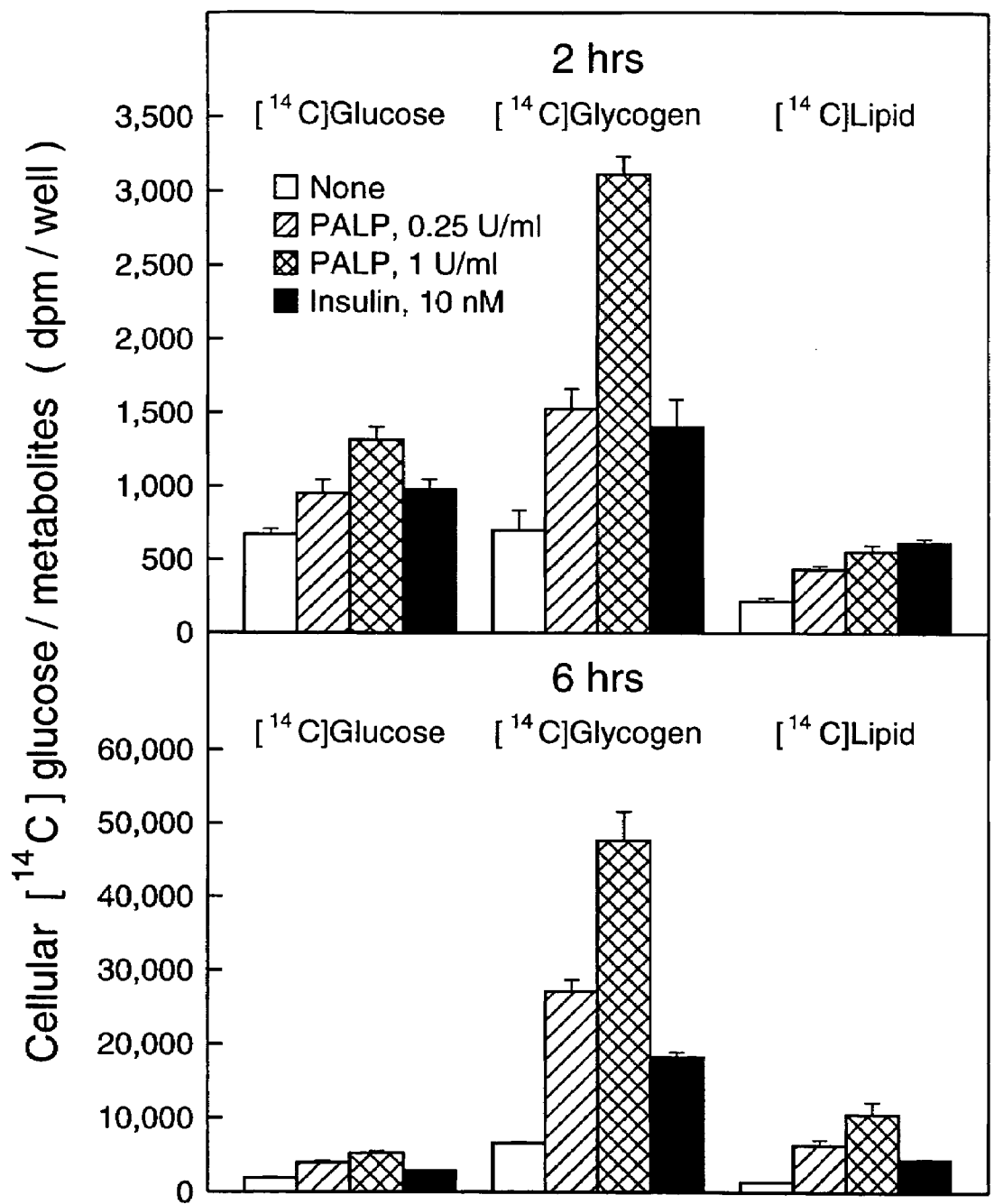
FIG. 12 indicates that in differentiated L1 adipocytes, 1 U/mL commercial PALP is-more effective than 10 nM insulin in enhancing cellular uptake of D-[$^{14}$C]glucose, as well as metabolism of the radiolabeled glucose to form glycogen and lipids, at both 2 hours and 6 hours after treatment.

Effect of PALP and Ins on the Cellular Uptake and Metabolism of Glucose in Differentiated L1 Cells Differentiated L1 cells in 12-well plates were incubated in 2% FBS-containing glucose-free DMEM with 1 µCi/mL of D-[$^{14}$C]glucose for 2 hours (FIG. 12, upper panel or 6 hours (FIG. 12, lower paned in the absence (□) or presence of 0.25 U/mL commercial PALP (◐), 1 U/mL commercial PALP (◉), or 10 nM Ins (■). The data shown in FIG. 12 are the mean±S.D. of three determinations in one experiment (the experiment was repeated once with similar results). Note that on this occasion, the concentration of Ins was only 10 nM, which is closer (although still higher to the physiological concentration of Ins (around 1 nM or less).

After treatments for 2 hours, 1 U/mL PALP had soft grater effects than Ins on the cellular level of D-[$^{14}$C]glucose and [$^{4}$C]glycogen (upper panel. After incubations for 6 hours, 1 U/mL of PALP was more effective than 10 nM Ins in stimulating uptake of D-[$^{14}$C]glucose and its subsequent conversion into both [$^{14}$C]glycogen and [$^{14}$C]total lipid (lower panel).

Example 17

Figure 13:
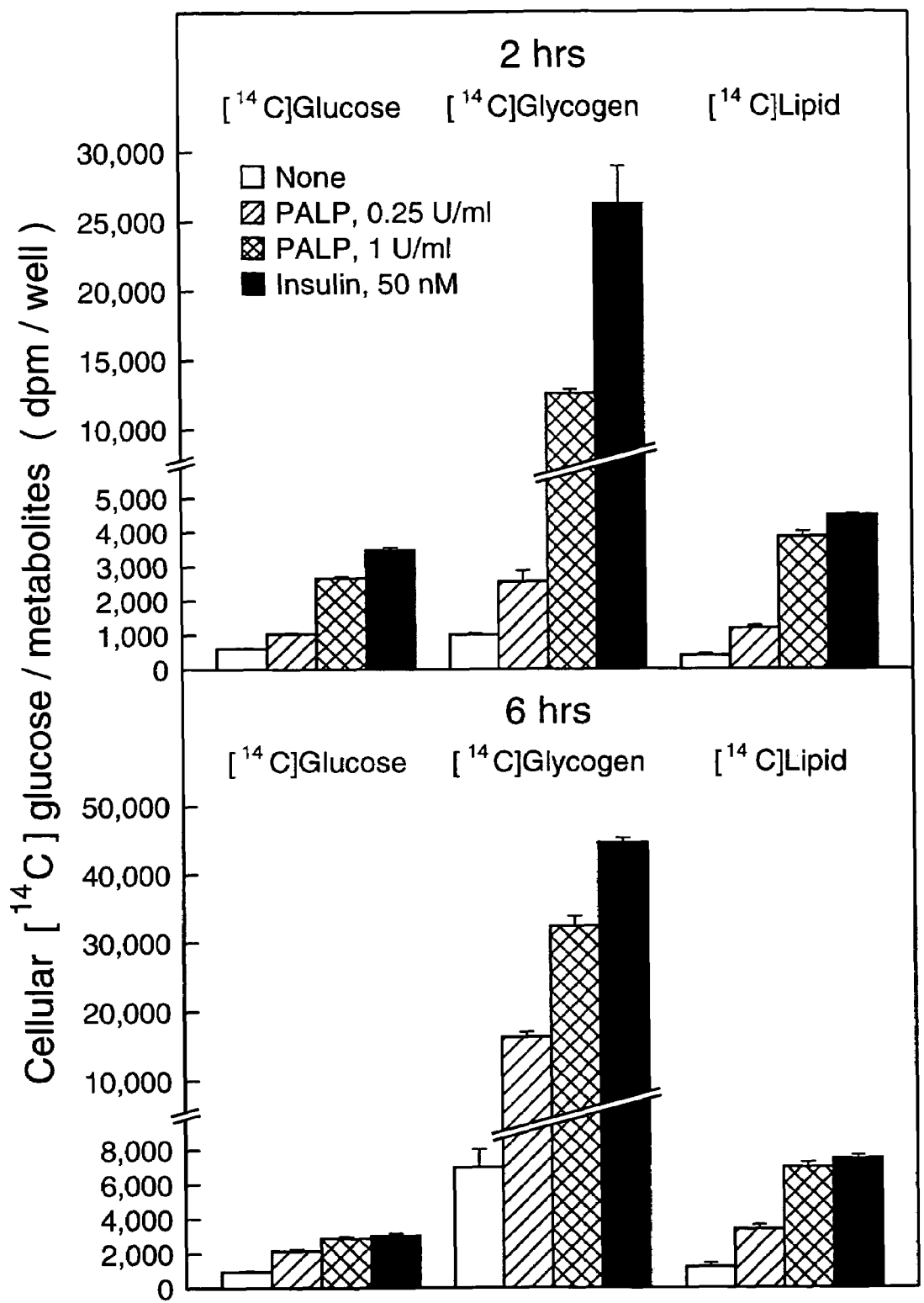
FIG. 13 demonstrates that in differentiated L1 adipocyces, 1 U/mL commercial PALP is somewhat less effective than 50 nM (supraphysiological) insulin in stimulating uptake and metabolism of D-[$^{14}$C]glucose, at both 2 hours and 6 hours after treatment.

Comparison of the Effects of PALP and a High Concentration of Ins on the Cellular Uptake and Metabolism of Glucose in Differentiated L1 cells Differentiated L1 cells in 12-well plates were incubated in 2% FBS-containing glucose-free DMEM for 2 hours (FIG. 13, upper panel or 6 hours (FIG. 13, lower panel with 1 μCi/mL of D-[$^{14}$C]glucose in the absence (□) or presence of 0.25 U/mL commercial PALP (◐), U/mL commercial PALP (◉), or 50 nM Ins (■). The data shown in FIG. 13 are the mean±S.D. of three determinations in one experiment (the experiment was repeated once with similar results).

After incubations for either 2 hours (FIG. 13, upper panel) or 6 hours (FIG. 13, lower panel), 50 mM Ins was significantly more effective than 1 U/mL of PALP on [$^{14}$C]glycogen synthesis and slightly more effective on [$^{14}$C]total lipid synthesis and the cellular content of D-[$^{14}$C]glucose.

Example 18

Figure 14:
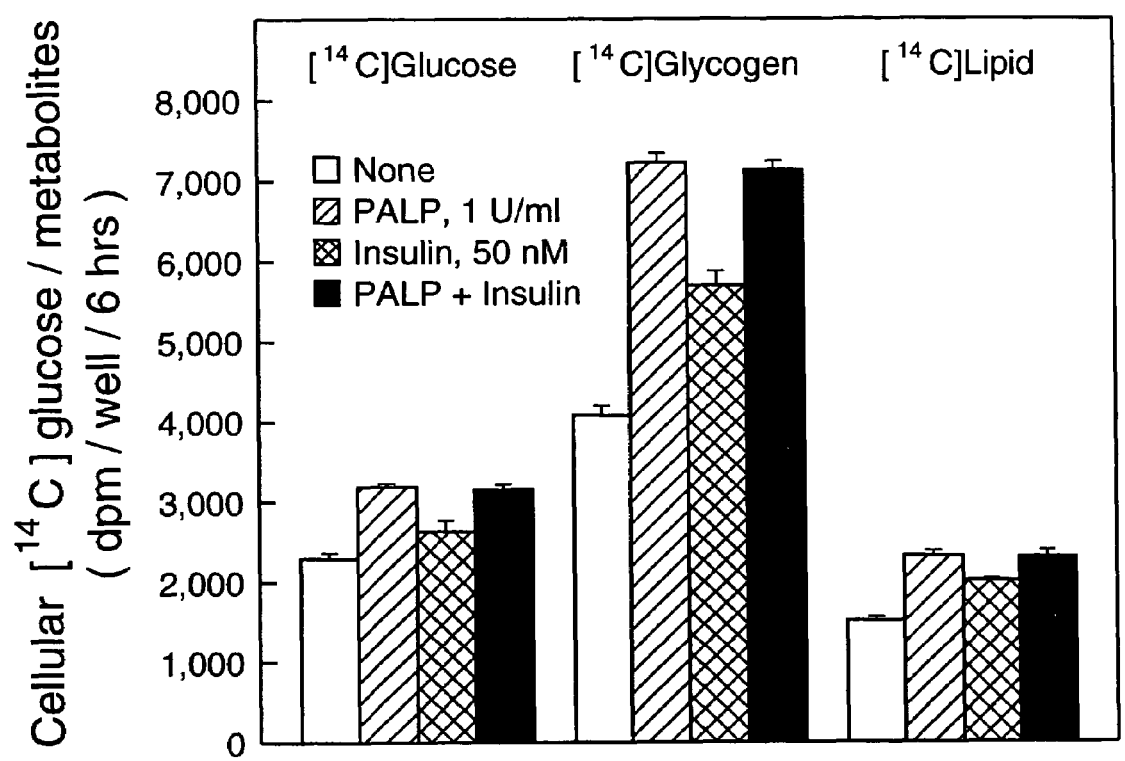
FIG. 14 demonstrates that in mouse embryo NIH 3T3 fibroblasts, commercial PALP is more effective than insulin in stimulating uptake and metabolism of D-$^{14}$C]glucose, and that insulin does not modify the effect of PALP when used in combination with PALP.

Comparison of Stimulation of Glucose Uptake and Metabolism in Mouse Embryo NIH 3T3 Fibroblasts by PALP and Ins Data shown in FIG. 14 is for an experiment comparing the effects of PALP and Ins on glucose metabolism in mouse embryo NIH 3T3 fibroblasts. This cell line was chosen because it is relatively insensitive to Ins, and, therefore, it appeared to be suitable to further verify what had been suggested by animal experiments; namely, that the effects of PALP occur independently of Ins. Since serum may contain Ins, the fibroblasts were incubated in serum-free medium to further exclude any contribution by Ins.

Accordingly, confluent NIH 3T3 fibroblast cultures in 12-well plates were incubated for 5 hours in serum-free glucose-free DMEM with 1 μCi/mL of D-[$^{14}$C]glucose in the absence (□) or presence of 1 U/mL commercial PALP (◐), 50 nM Ins (◉), or 1 U/mL commercial PALP+50 nM Ins (■). The data shown in FIG. 14 are the mean±S.D. of three determinations in one experiment (the experiment was repeated once with similar results).

PALP enhanced cellular uptake of D-[$^{14}$C]glucose by 38% and its metabolism to [$^{14}$C]glycogen and [$^{14}$C]total lipid by 77% and 55%, respectively. In each case, treatment with Ins alone (◉) was only about 50% as effective as PALP alone (◐), and Ins did not enhance any of the effects of PALP when used in combination (■), relative to treatment by PALP alone (◐). Thus, this experiment demonstrates that PALP exerts an effect on glucose metabolism without requiring the presence of insulin.

Examples 19 and 20

Effects of PALP Preparations on Glucose Metabolism in Differentiated L1 Cells in the Presence of 10% Serum In the presence of 10% FBS most cellular events, particularly cell proliferation, are maximally or near maximally stimulated due to the presence of optimum concentrations of growth factors. It is difficult to assess which serum level (2% or 10% serum) used for in vitro experiments corresponds better to the situation in vivo (which, in turn, will also depend on the eating habit and the combination of various physiological parameters of the individual). However, as a conservative approach, it is generally accepted that if an effect can be observed in vitro even in the presence of 10% serum, then it is very likely that this particular phenomenon is physiologically relevant. Therefore, next it was determined if PALP and Ins still can enhance glucose metabolism in the presence of 10% serum, and if the effects of preparations made from various batches of commercial PALP were comparable.

Example 19

Figure 15:
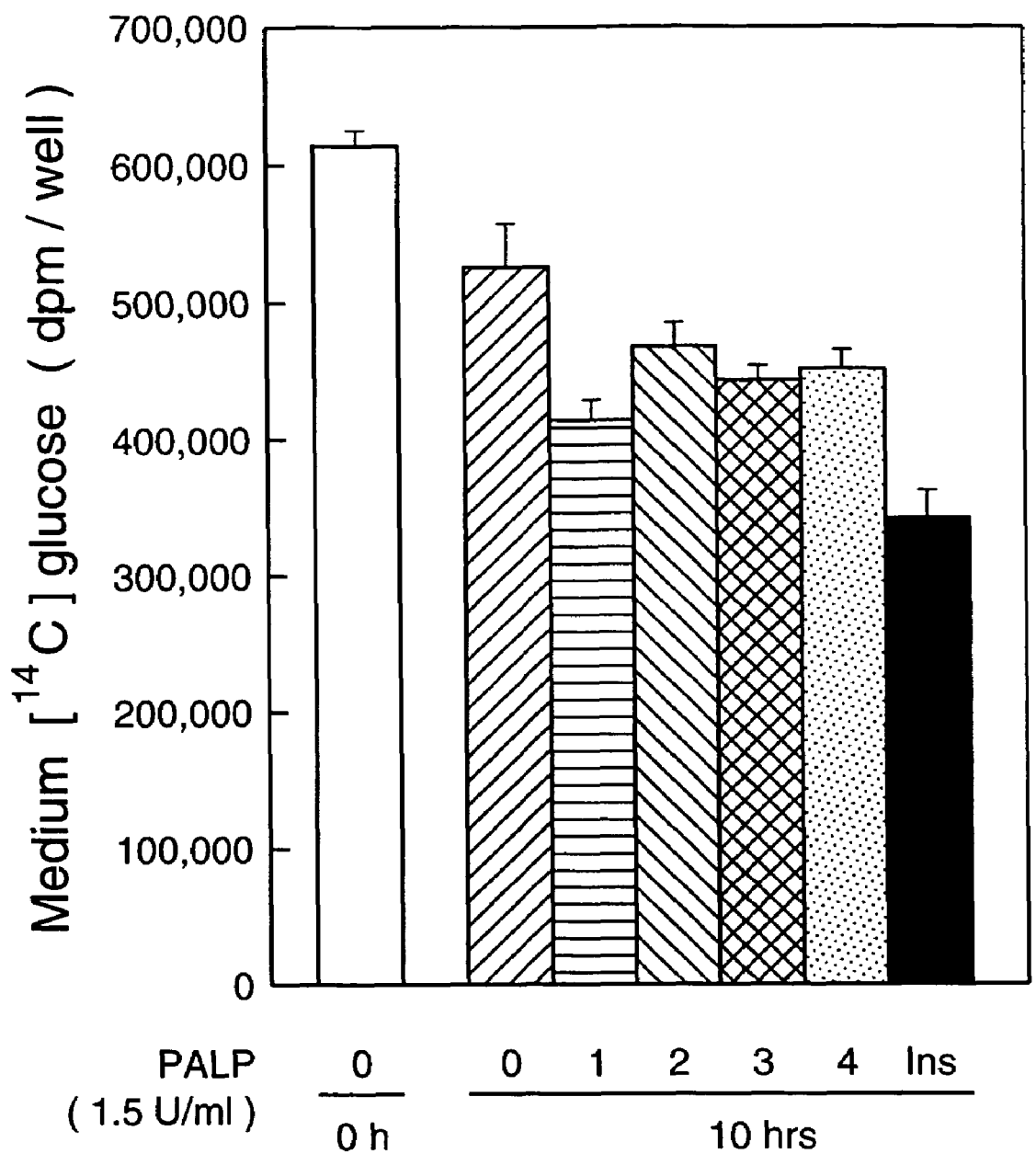
FIG. 15 indicates that in differentiated L1 adipocytes, preparations made from different batches of commercial PALP (each preparation containing 1.5 U/mL) have effects on the loss of D-[$^{14}$C]glucose from incubation medium that include some variability which appears to be larger than the inter-experimental error. Each of the preparations was somewhat less effective than 50 nM insulin.

Effect of PALP Preparations and Ins on Glucose Content of Incubation Medium for Differentiated L1 Cells Data shown in FIG. 15 is for an experiment in which the effects of four different preparations made from various batches of commercially obtained PALP on the loss of D-[$^{14}$C]glucose from the incubation medium in differentiated L1 cell cultures were compared to the effect of Ins.

Preparations were made from four separate batches of commercially obtained PALP (preparations 1 through 4), the preparations comprising 1.5 U/mL PALP in serum-free glucose-free DMEM. Differentiated L1 cells were pretreated for 30 minutes with PALP-free DMEM (◐), with preparation 1 (◉), 2 (◉), 3 (◉), or 4 (◻), or with 50 nM Ins in serum-free glucose-free DMEM (■), followed by the addition of 0.5 μCi of D-[$^{14}$C]glucose for 10 hours. The data shown in FIG. 15 are [$^{14}$C]glucose content of the incubation medium at the end of incubation (time=10 hours), compared to [$^{14}$C]glucose content at the start of incubation (time=0 hours; □), and represent the mean±S.D. of three determinations in one experiment (the experiment was repeated once with similar results).

While all four PALP preparations clearly enhanced the loss of D-[$^{14}$C]glucose from the medium, there was some variability in their respective effects which appeared to go beyond the experimental error. Again, 50 nM Ins was more effective than any of the commercial PALP preparations.

Example 20

Figure 16:
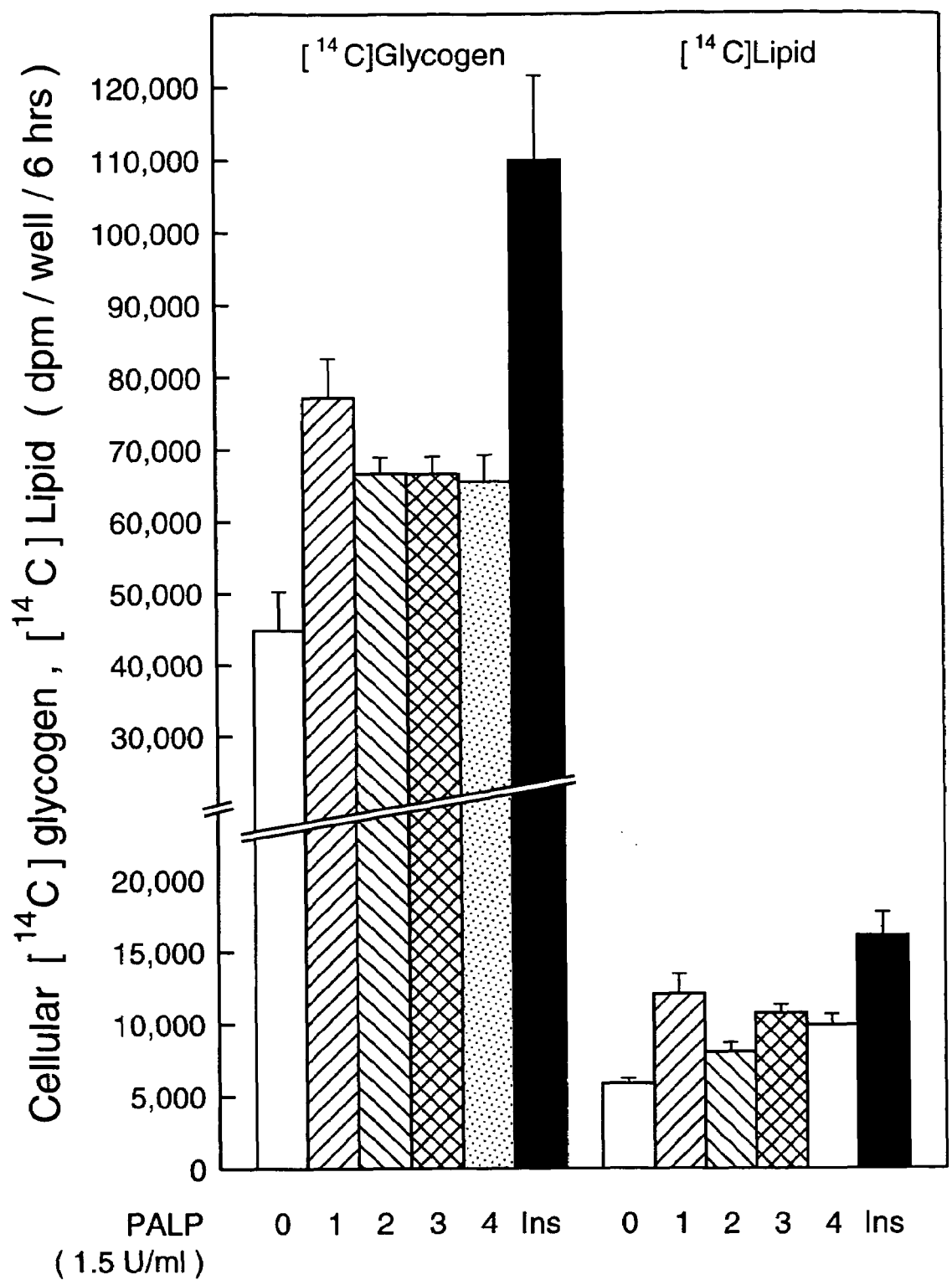
FIG. 16 indicates that in differentiated L1 adipocytes, preparations made from different batches of commercial PALP have effects on the synthesis of glycogen and lipids from D-[$^{14}$C]glucose that include some variability.

Exploration of the Differences in Effect on Glucose Metabolism for Various PALP Preparations Data shown in FIG. 16 is for an experiment in which potential differences in the effects on glucose metabolism in differentiated L1 cells among the four commercial PALP preparations was further explored. Differentiated L1 cells were pretreated (in 10% FBS-containing medium) for 30 min with PALP-free DMEM (□), or with preparation 1 (▨), 2 (▧), 3 (▨), or 4 (▩) of commercial PALP (1.5 U/mL), or 50 nM Ins in serum-free glucose-free DMEM (■), followed by the addition of 0.5 µCi of D-[$^{14}$C]glucose for 6 hours. The data are the mean±S.D. of three determinations in one experiment (the experiment was repeated once with similar results).

While, again, each PALP preparation enhanced the synthesis of both [$^{14}$C]glycogen and [$^{14}$C]total lipid, the preparation which decreased the medium content of D-[$^{14}$C]glucose the most (PALP 1 in FIG. 15) was also the most effective in stimulating the synthesis of [$^{14}$C]glycogen and [$^{14}$C]total lipid (FIG. 16).

In addition to demonstrating variability in the actions of various batches of commercially obtained PALP, the data in FIGS. 15 and 16 also indicate that PALP exerts considerable effects on glucose metabolism in L1 cells even in the presence of 10% serum. Such effects of PALP were observed in the presence of 10% serum only if cells were used 8-12 days after terminating the differentiation treatment.

Example 21 and 22

Effect of Homogeneous Purified PALP on Glucose Metabolism in Differentiated L1 Cells In the experiments described in Examples 21 and 22, homogeneous purified PALP was used to demonstrate that the effects of partially purified commercial PALP that were observed in preceding Examples were indeed elicited by activity of the PALP enzyme and not by a contaminating protein.

Homogeneous purified PALP was prepared by the complete purification procedure described in Example 1. The homogeneous purified PALP used in the experiments of Examples 21 and 22 produces a single band in an electrophoretic separation, such as shown in lane 5 of FIG. 1.

Example 21

Figure 17:
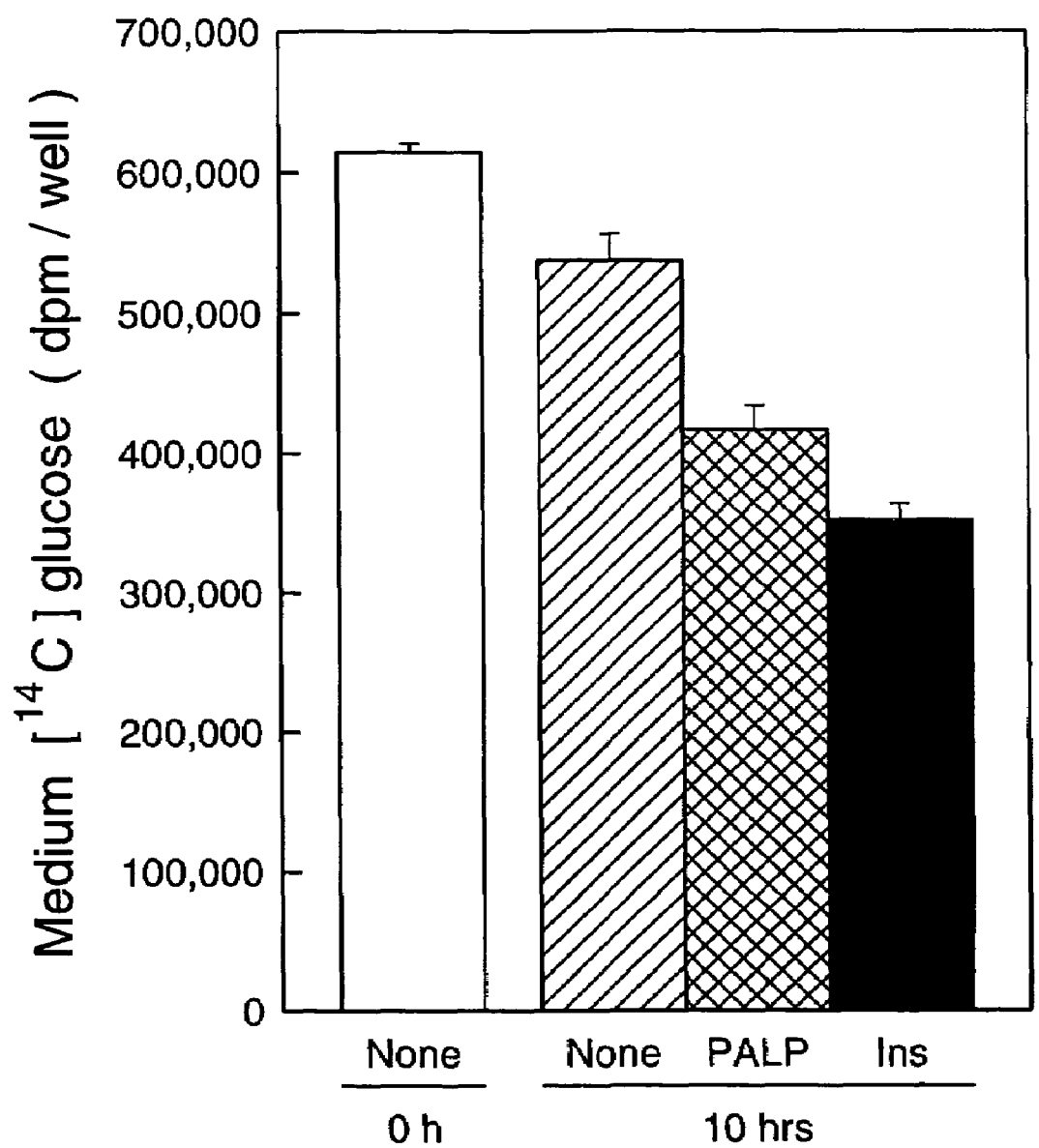
FIG. 17 demonstrates that in differentiated L1 adipocytes, homogeneous purified PALP is somewhat less effective than insulin in reducing the amount of D[$^{14}$C]glucose in incubation medium.

Effect of Homogeneous Purified PALP on Glucose Content of Incubation Medium in Differentiated L1 Cells Data for this Example is shown in FIG. 17. Differentiated L1 cells in 12-well plates were incubated in 10% serum-containing glucose-free DMEM for 10 hours with 0.5 µCi of D-[$^{14}$C]glucose in the absence (▨) or presence of 200 nM homogeneous purified PALP (▧), or 50 nM Ins (■), followed by the determination of D-[$^{14}$C]glucose in the medium. The data shown in FIG. 17 are [$^{14}$C]glucose content of the incubation medium at the end of incubation (time=10 hours), compared to [$^{14}$C]glucose content at the start of incubation (time=0 hours; □), and represent the mean±S.D. of three determinations in one experiment.

Homogeneous purified PALP at 200 nM effectively reduced the medium content of D-[$^{14}$C]glucose, although its effect was somewhat less than that of 50 nM insulin. The effects of purified PALP on glucose uptake were comparable to the effects of the best commercial PALP preparation demonstrated in Example 19 (FIG. 15).

Example 22

Figure 18:
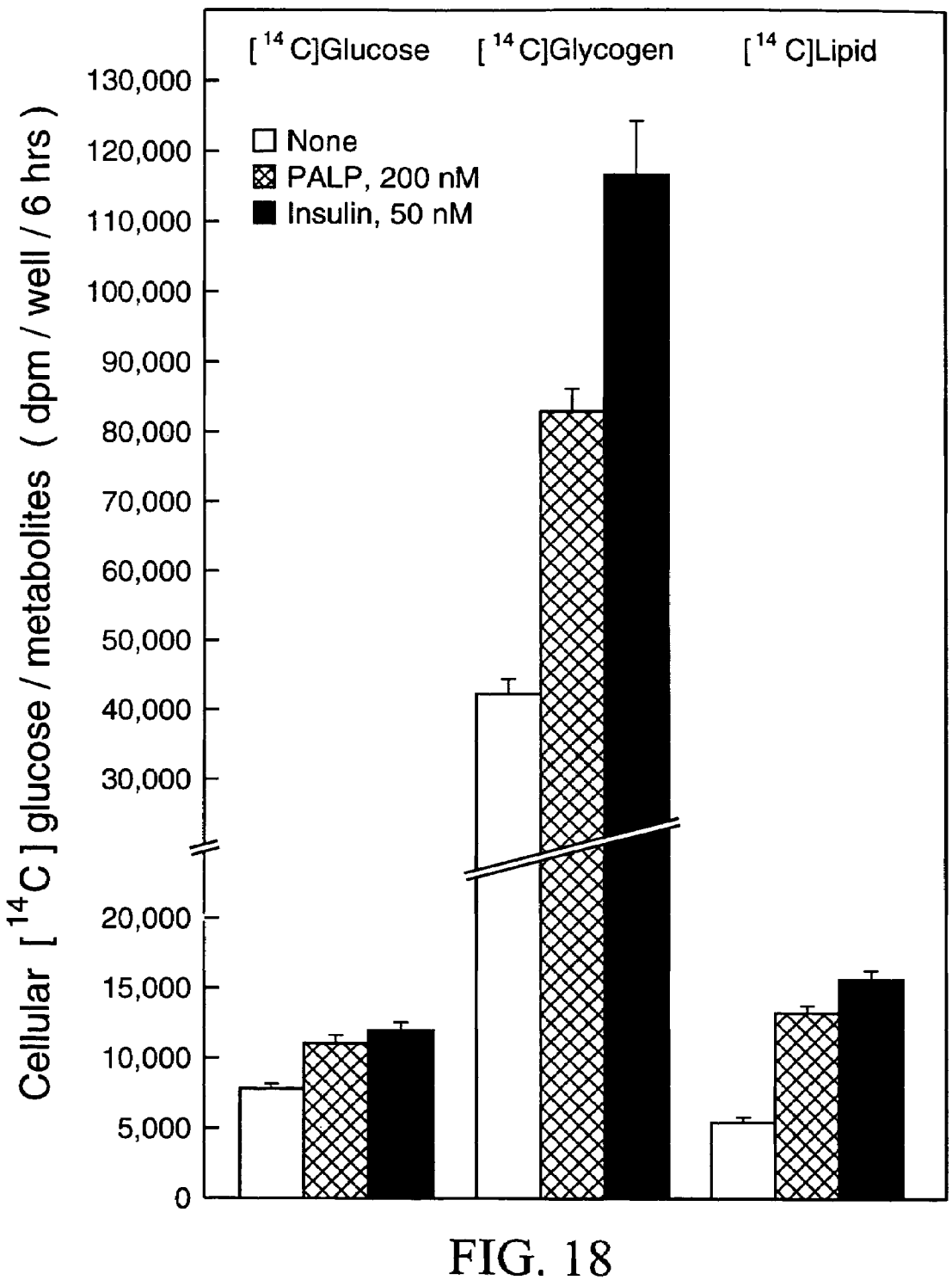
FIG. 18 demonstrates that in differentiated L1 adipocytes, homogeneous purified PALP is somewhat less effective than insulin in enhancing uptake and metabolism of D-[$^{14}$C]glucose.

Effect of Homogeneous Purified PALP on Glucose Uptake and Metabolism for Differentiated L1 Cells Data for this Example is shown in FIG. 18. Homogeneous PALP was used to demonstrate that the observed effects of PALP on the cellular uptake and metabolism of D-[$^{14}$C]glucose from prior Examples was indeed mediated by the PALP enzyme. Differentiated L1 cells in 12-well plates were incubated in 10% serum-containing glucose-free DMEM for 6 hours with 0.5 µCi of D-[$^{14}$C]glucose in the absence (Q) or presence of 200 nM homogeneous purified PALP (▧), or 50 nM Ins (■). The data are the mean±S.D. of three determinations in one experiment.

Homogeneous PALE increased cellular content of D-[$^{14}$C] glucose 1.4-fold, increased synthesis of [$^{14}$C]glycogen 1.95fold, and increased [$^{14}$C]total lipid 2.45-fold. Again, the effects of homogeneous purified PALP were comparable to the effects of the less pure commercial PALP preparations demonstrated in Example 20 (FIG. 16). Overall, it seems clear that the reproducible effects of PALP are the best assured if PALP is purified to homogeneity.

Example 23

Effect of α-antitrypsin on Glucose Levels in the Glucose Tolerance Test

α-antitrypsin is the major contaminant of the commercially obtained PALP [Q. B. -She, J. J. Mukherjee, K. S. Crilly, and Z. Kiss, "α-antitrypsin can increase insulin-induced mitogenesis in various fibroblast and epithelial cell lines." *FEBS Letters* 473, 33-36 (2000)]. Therefore, an experiment was performed to determine whether α-antitiypsin has PALP-like effects on blood glucose levels. A glucose tolerance test was performed as generally described in Example 2. In the experiment, highly purified α-antitrypsin was administered either intraperitoneally or subcutaneously at a quantity of 2 mg/mouse, 24 hours prior to administration of glucose.

α-antitrypsin failed to lower the blood glucose level (data not shown). This observation indicates that α-antitrypsin did not mediate the effect on blood glucose levels that were observed for administration of commercial PALP.

Example 24

PALP-antibody Blocks the Effects of Homogeneous Purified PALP on Glucose Metabolism Even the homogeneous purified PALP preparation used in Examples 21 and 22 still might have contained a very small amount of an active contaminant which escaped detection. To rule out this possibility, a PALP-specific antibody (polyclonal rabbit anti-PALP from Zymed Laboratories, South San Francisco, Calif.) was used to block the effect of the PALP enzyme.

Figure 19:
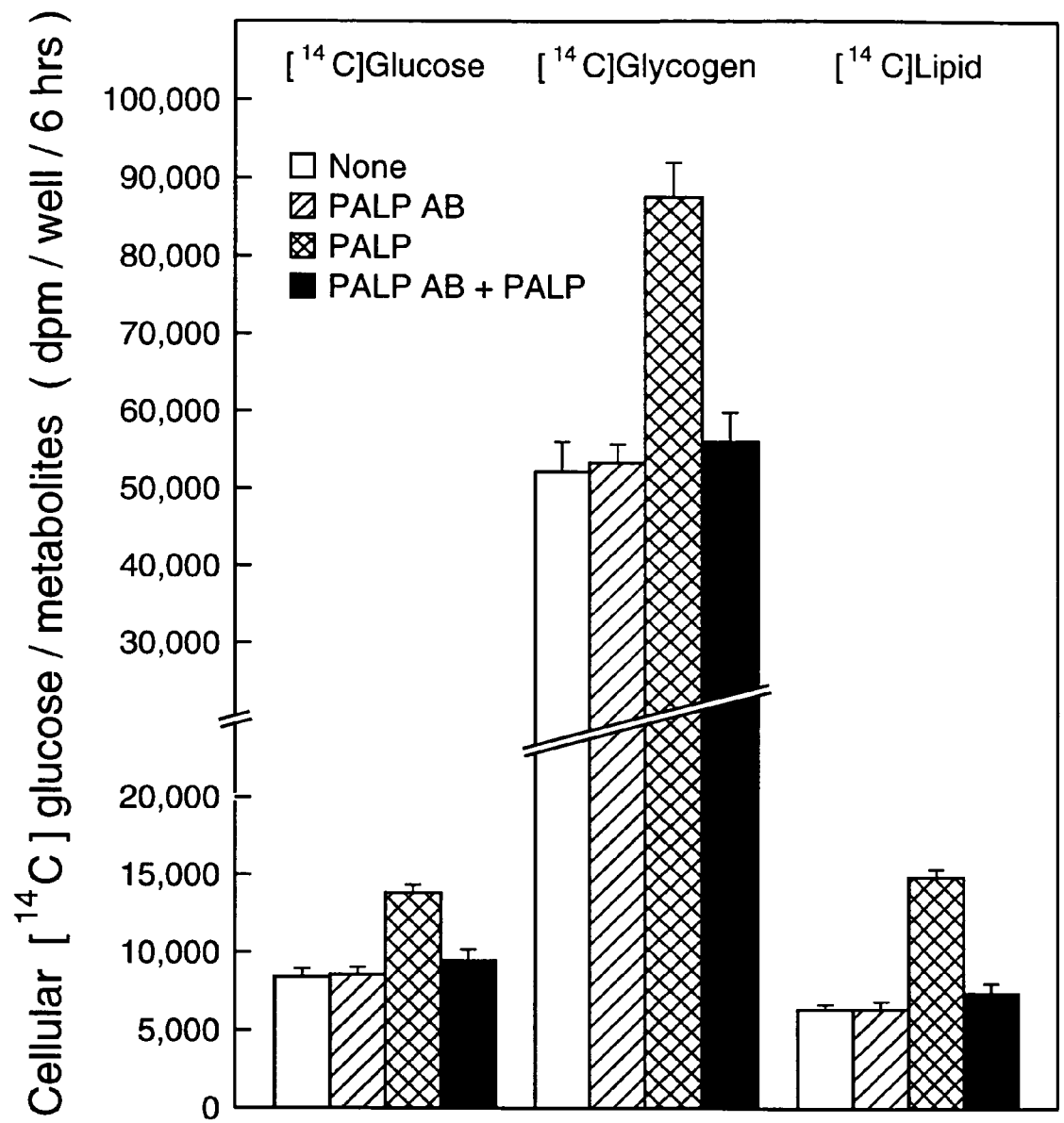
FIG. 19 demonstrates that in differentiated L1 adipocytes, an antibody against PALP is capable of inhibiting all effects of homogeneous purified PALP on the uptake and metabolism of D-[$^{14}$C]glucose.

Data from the experiment is shown in FIG. 19. Differentiated L1 cells in 12-well plates were incubated in 10% serum-containing glucose-free DMEM for 6 hours in the absence (□) or presence of 30 µg/mL of PALP-antibody (●), 15 µg/mL of homogeneous purified PALP (◨), or 30 µg/mL of PALP-antibody +15 µg/mL of homogeneous purified PALP (■). The data are the mean±S.D. of three independent determinations in one experiment.

While PALP-antibody alone had no effect on glucose metabolism, PALP-antibody clearly blocked the stimulatory effects of homogeneous purified PALP on the uptake of D-[$^{14}$C]glucose, as well as the synthesis of [$^{14}$C]glycogen and [$^{14}$C]total lipids. Thus, this experiment provides conclusive proof that the effects on glucose metabolism observed with commercial PALP preparations and homogeneous purified PALP preparations were indeed mediated by the PALP enzyme.

Based on these data, the conclusion can be made that in the reported in vivo experiments (Examples 2—8), the inhibitory effects of commercial PALP on the elevation of blood glucose level were mediated by the PALP enzyme. The present invention may thus provide an effective new treatment for diabetes that would meet each criterion listed above. In particular, the experiments presented in the Examples indicate that treatment regimens including the administration of PALP would not cause weight gain and could diminish weight loss. Furthermore, the experiments presented indicate that the active agent (PALP) acts via mechanism(s) that are independent from the actions of insulin, and that the active agent is metabolically stable, which permits less frequent usage. Finally, the results suggest that PALP may prolong the life of severely diabetic patients.

The invention described herein includes purified human placental alkaline phosphatase for use in a medicament. The invention further includes purified human placental alkaline phosphatase for use in a medicament for the treatment of diabetes. The invention includes the use of purified human placental alkaline phosphatase for the manufacture of a medicament for the treatment of diabetes. The invention further includes use of purified human placental alkaline phosphatase for the manufacture of a medicament for reducing blood glucose level.

This invention may take on various modifications and alterations without departing from the spirit and scope thereof. Accordingly, it is to be understood that this invention is not to be limited to the above-described, but it is to be controlled by the limitations set forth in the following claims and any equivalents thereof. It is also to be understood that this invention may be suitably practiced in the absence of any element not specifically disclosed herein.

In describing preferred embodiments of the invention, specific terminology is used for the sake of clarity. The invention, however, is not intended to be limited to the specific terms so selected, and it is to be understood that each term so selected includes all technical equivalents that operate similarly.

What is claimed is:

1. A method of reducing blood glucose level in a non-obese or obese human exhibiting chronically elevated blood glucose level or already afflicted with Type 2 diabetes, comprising the step of administering a therapeutically effective amount of purified human placental alkaline phosphatase, or an active derivative thereof.

2. The method of claim 1 wherein the step of administering is performed by intravenous, subcutaneous, intraperitoneal, intramuscular, or intradermal injection of a preparation comprising:
   a) a physiologically acceptable carrier; and
   b) the purified human placental alkaline phosphatase or active derivative thereof, dissolved or dispersed in the carrier.

3. The method of claim 2 wherein the preparation comprises homogeneous, purified human placental alkaline phosphatase.

4. The method of claim 1 wherein the administering of human placental alkaline phosphatase or active derivative thereof is effective to reduce the human's blood glucose level to below about 10 mM.

5. The method of claim 1 wherein the administering of human placental alkaline phosphatase or active derivative thereof is effective to reduce the human's blood glucose level to below about 8 mM.

6. The method of claim 1 wherein the administering of human placental alkaline phosphatase or active derivative thereof is effective to reduce the human's blood glucose level to within the range of about 4 mM to about 7 mM.

7. The method of claim 1 wherein the method further comprises administering an anti-diabetic medicament in combination with the human placental alkaline phosphatase or active derivative thereof.

8. The method of claim 7 wherein the anti-diabetic medicament is an insulin secretagogue, a biguanide, an inhibitor of α-glucosidase, a thiazolidinedione, insulin or NN2211.

9. The method of claim 1 wherein the administering includes three alternative courses i) prior to an expected glucose load, ii) about 12 hours prior to an expected glucose load, or iii) about 24 hours prior to an expected glucose load.

10. The method of claim 1, wherein the step of administering includes periodically administering to the human the therapeutically effective amount of purified human placental alkaline phosphatase, or an active derivative thereof.

11. The method of claim 10 further comprising periodically administering an anti-diabetic medicament in combination with the human placental alkaline phosphatase or active derivative thereof.

12. The method of claim 10 wherein the periodic administering includes four alternative courses i) about once per two weeks, ii) about once per week, iii) about twice per week, or iv) about once per day.

13. The method of claim 10 wherein the therapeutically effective amount is in the range of about 0.2 grams to about 3 grams per square meter of calculated body surface area of the human.

14. The method of claim 10 wherein the therapeutically effective amount is in the range of about 0.2 grams to about 1 gram per square meter of calculated body surface area of the human.

15. The method of claim 10 wherein the therapeutically effective amount is in the range of about 1 gram to about 3 grams per square meter of calculated body surface area of the human.

16. The method of claim 10 wherein the periodically administering is performed by intravenous, subcutaneous, intraperitoneal, intramuscular, or intradermal injection of a preparation comprising:
   a) a physiologically acceptable carrier; and
   b) the human placental alkaline phosphatase or active derivative thereof, dissolved or dispersed in the carrier.

17. The method of claim 16 wherein the human placental alkaline phosphatase or active derivative thereof includes homogeneous, purified human placental alkaline phosphatase extracted from human tissue, produced by a recombinant method, or chemically synthesized.

18. The method of claim 1 wherein the human placental alkaline phosphatase or active derivative thereof includes homogeneous, purified human placental alkaline phosphatase produced by a recombinant method.

* * * * *